US011635859B2

(12) United States Patent
Sato et al.

(10) Patent No.: US 11,635,859 B2
(45) Date of Patent: Apr. 25, 2023

(54) ELECTRONIC APPARATUS WITH ELECTRODE SUBSTRATE THAT GENERATES OZONE

(71) Applicant: WUHAN TIANMA MICRO-ELECTRONICS CO., LTD., Wuhan (CN)

(72) Inventors: Tetsushi Sato, Kanagawa (JP); Hiroshi Haga, Kanagawa (JP); Daisuke Sugimoto, Kanagawa (JP)

(73) Assignee: WUHAN TIANMA MICRO-ELECTRONICS CO., LTD., Wuhan (CN)

( * ) Notice: Subject to any disclaimer, the term of this patent is extended or adjusted under 35 U.S.C. 154(b) by 0 days.

(21) Appl. No.: 17/509,602

(22) Filed: Oct. 25, 2021

(65) Prior Publication Data

US 2022/0129112 A1 Apr. 28, 2022

(30) Foreign Application Priority Data

Oct. 27, 2020 (JP) .............................. JP2020-179996

(51) Int. Cl.
 *G06F 3/044* (2006.01)
 *G06F 3/041* (2006.01)
(52) U.S. Cl.
 CPC .......... *G06F 3/0441* (2019.05); *G06F 3/0412* (2013.01)

(58) Field of Classification Search
 CPC ............................ G06F 3/0441; G06F 3/0412
 See application file for complete search history.

(56) References Cited

U.S. PATENT DOCUMENTS

| 2015/0103024 | A1* | 4/2015 | Haga | ...................... G06F 3/0448 |
| | | | | 345/173 |
| 2016/0154462 | A1* | 6/2016 | Haga | ....................... G06F 3/016 |
| | | | | 345/174 |

FOREIGN PATENT DOCUMENTS

JP 2014-186900 10/2014

* cited by examiner

*Primary Examiner* — Lisa S Landis
(74) *Attorney, Agent, or Firm* — Nixon & Vanderhye

(57) ABSTRACT

An electronic apparatus includes an electrode substrate that has a transparent first electrode and a transparent second electrode that are provided on one surface of a transparent insulating substrate, and an insulating film that electrically insulates the first electrode from the second electrode, the electrode substrate being configured so as to cover a surface of a display medium where an image is displayed; and a driver circuit that is connected to the electrode substrate and generates an electric field between the first electrode and the second electrode by applying a voltage to the first electrode and the second electrode.

19 Claims, 21 Drawing Sheets

ELECTRONIC APPARATUS WITH ELECTRODE SUBSTRATE THAT GENERATES OZONE

CLAIM OF PRIORITY

The present application claims priority from Japanese patent application JP 2020-179996 filed on Oct. 27, 2020, the content of which is hereby incorporated by reference into this application.

BACKGROUND

The present invention pertains to an electronic apparatus.

JP2014-186900 discloses a discharge element capable of suppressing dielectric breakdown due to an AC high voltage for enerating a plasma discharge, and a method of manufacturing the same. The discharge element includes an insulating substrate, an electrode, and an insulating film. The insulating substrate is formed of heat-resistant glass or ceramic. The electrode is formed on the insulating substrate and is applied with an AC high voltage. The insulating film covers the electrode. The insulating substrate and the insulating film are formed so that the discharge starting voltage on that surface side of the insulating substrate which faces the electrode is lower than the discharge starting voltage on that surface side of the insulating film which faces the electrode.

When ozone is generated in the discharge element, an external power supply is connected to the pad 3P1 and the pad 3P2 to apply an AC high voltage. In the discharge element, the discharge start voltage is lower on the surface closer to the insulating substrate than on the surface on the insulating film side. Therefore, when an AC high voltage applied from an external power source is gradually increased, a discharge is started on the surface of the insulating substrate side, and plasma is generated. By this plasma, oxygen in the air is decomposed and bonded to generate ozone (see the paragraph [0031] in JP2014-186900).

Regarding electronic apparatuses with which a person can come into contact such as a display device or a tactile presentation device, in order to disinfect sections thereof with which a person can come into contact, a disinfection device such as a disinfectant spray or an ozone generator needs to be separately provided. Also, conventional ozone sources have a low permeability due to the shape thereof or metals used for the electrodes. Thus, it would be difficult to attach the ozone source to sections of the electronic apparatus with which a person could come into contact.

SUMMARY

First aspect of the invention disclosed in this application is an electronic apparatus, comprising: an electrode substrate that has a transparent first electrode and a transparent second electrode that are provided on one surface of a transparent insulating substrate, and an insulating film that electrically insulates the first electrode from the second electrode, the electrode substrate being configured so as to cover a surface of a display medium where an image is displayed; and a driver circuit that is connected to the electrode substrate and generates an electric field between the first electrode and the second electrode by applying a voltage to the first electrode and the second electrode.

Second aspect of the invention disclosed in this application is an electronic apparatus, comprising: an electrode substrate that has a transparent first electrode and a transparent second electrode that are provided on one surface of a transparent insulating substrate, and a first insulating film that electrically insulates the first electrode from the second electrode; a display medium in which a display surface that displays an image is covered by the electrode substrate; a first driver circuit that is connected to the electrode substrate and drives the electrode substrate as an ozone source by applying a voltage to the first electrode and the second electrode; a second driver circuit that is connected to the electrode substrate and drives the electrode substrate as a touch sensor by applying a voltage to the first electrode and the second electrode; and a selection circuit that switches between the first driver circuit and the second driver circuit.

Third aspect of the invention disclosed in this application is an electronic apparatus, comprising: an electrode substrate that has a transparent first electrode and a transparent second electrode that are provided on one surface of a transparent insulating substrate, and an insulating film that electrically insulates the first electrode from the second electrode; a first driver circuit that is connected to the electrode substrate and drives the electrode substrate as an ozone source by applying a voltage to the first electrode and the second electrode; a second driver circuit that is connected to the electrode substrate and drives the electrode substrate as a touch sensor by applying a voltage to the first electrode and the second electrode; and a selection circuit that switches between the first driver circuit and the second driver circuit.

It is to be understood that both the foregoing general description and the following detailed description are exemplary and explanatory and are not restrictive of this disclosure.

DETAILED DESCRIPTION OF THE EMBODIMENTS

Below, electronic apparatuses according to Embodiments 1 to 7 will be described. The electronic apparatuses of Embodiments 1 to 7 can be used in touch sensors, display devices, display panels, and tactile presentation devices, for example. In the description below, the materials and numerical values such as the dimensions, voltages, and electric field intensities are merely examples, and other numerical values and materials may be used as long as these are within a scope enabling implementation.

Embodiment 1

Figure 1:
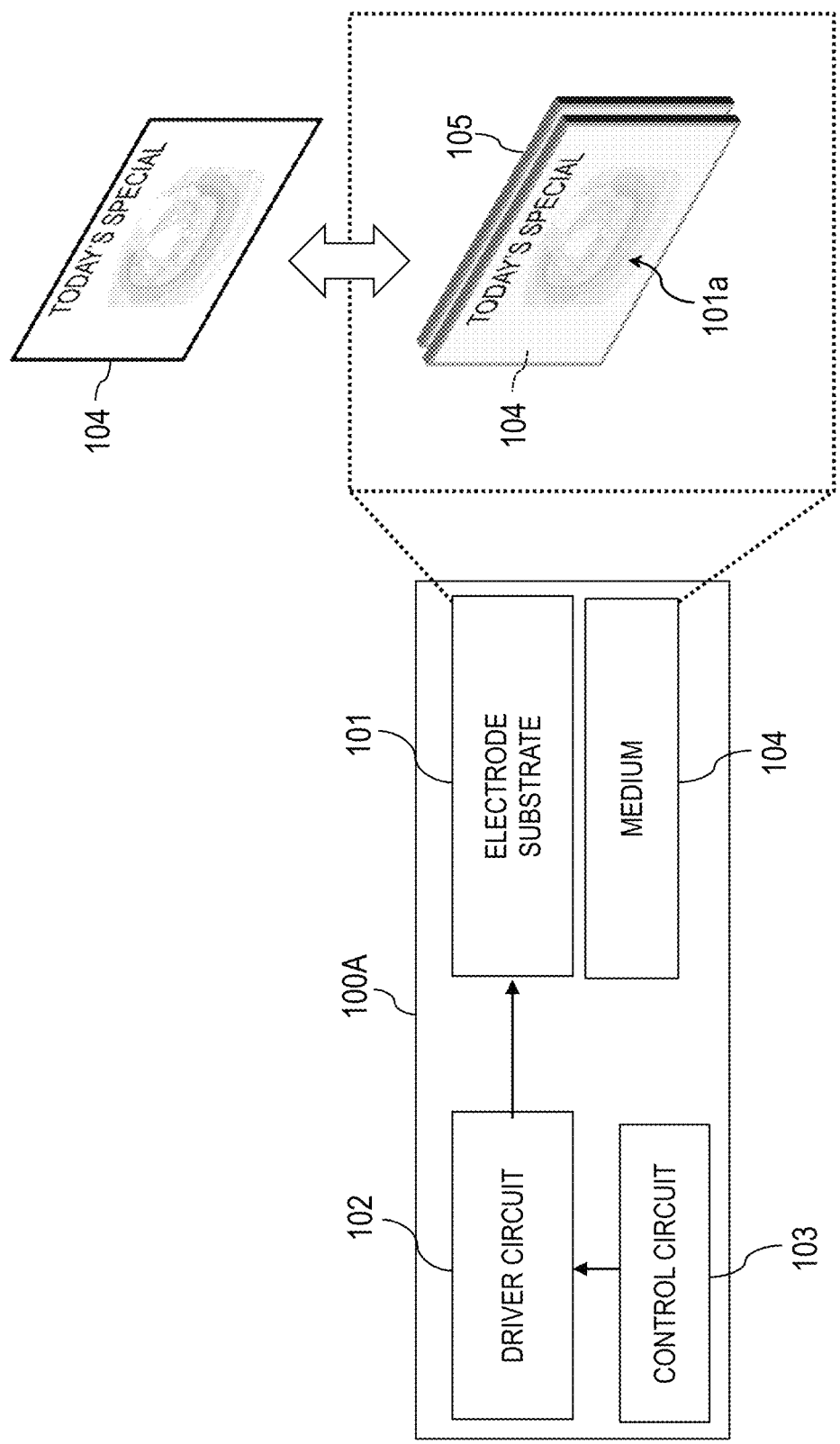
FIG. 1 illustrates an electronic apparatus according to Embodiment 1.

FIG. 1 illustrates an electronic apparatus according to Embodiment 1; the left side view in FIG. 1 is a block diagram showing a configuration example, and the right side view in FIG. 1 is a perspective view showing the structure. In Embodiment 1, an electronic apparatus 100A can be used in a display device using liquid crystal or organic EL technology or the like, or in a display panel that stores and displays photographs or the like. The electronic apparatus 100A has an electrode substrate 101, a driver circuit 102, a control circuit 103, and a display medium 104. The electrode substrate 101 is a substrate having one or more sets of two opposing electrodes, and is a substrate that generates ozone through the application thereto of a prescribed voltage.

Figure 2:
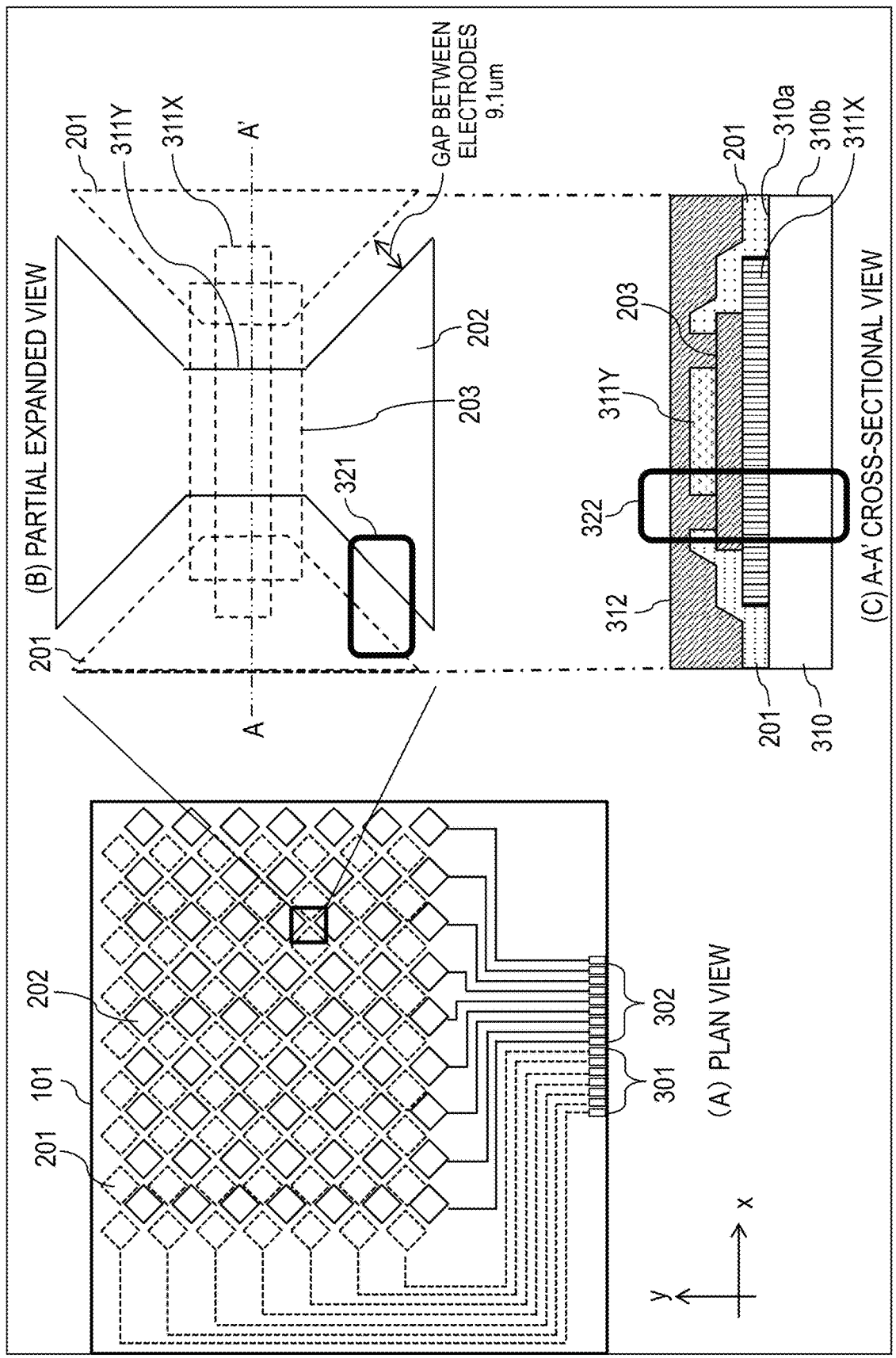
FIG. 2 illustrates the structure of the electrode substrate.

FIG. 2 illustrates the structure of the electrode substrate 101. A view (A) is a plan view of the electrode substrate 101. A view (B) is a partial expanded view of the plan view of (A). A view (C) is a cross-sectional view along the line A-A' of the partial expanded view of (B). The electrode substrate 101 has X electrodes 201, Y electrodes 202, and insulating films 203 that are disposed on a transparent support substrate 310.

In the views (A) and (B) in FIG. 2, the X electrodes 201 and wiring thereof are depicted with dotted lines, and the Y electrodes 202 and wiring thereof are depicted with solid lines. The X electrodes 201 and the Y electrodes 202 are transparent electrodes, and can be made of ITO (indium tin oxide), for example. The plan view shape of the X electrodes 201 and the Y electrodes 202 is quadrilateral (rhombus or rectangle), for example.

As shown in FIG. 1, the driver circuit 102 applies a prescribed voltage to the X electrodes 201 and the Y electrodes 202 to drive the electrode substrate 101 as an ozone source. Through the application of this voltage, ozone is generated on a surface 101a of the electrode substrate 101, thereby disinfecting the surface 101a of the electrode substrate 101.

The control circuit 103 controls the application of voltage by the driver circuit 102. Specifically, for example, the control circuit 103 issues commands to the driver circuit 102 to start or stop the application of voltage to the electrode substrate 101 according to a sensor (not shown) or an external input such as operations performed by a person.

As shown the right side view in FIG. 1, the surface of the display medium 104 where images are displayed is covered by the electrode substrate 101. The display medium 104 may be a medium (first display medium) where printed images (or hand-drawn/handwritten images) such as a menu or a photograph are displayed, or may be a medium (second display medium) in which the display medium 104 itself displays an image such as in the case of a liquid crystal display device or an organic EL display device.

As previously described, the X electrodes 201 and the Y electrodes 202 are transparent electrodes. The display medium 104 is inserted between the electrode substrate 101 and a back plate 105, for example. Accordingly, images can be viewed from the surface 101a. By using the electrode substrate 101 instead of the back plate 105, it is possible to generate ozone on both surfaces of the electronic apparatus 100A.

Next, the electrode substrate 101 will be described in detail. In the views (A) in FIG. 2, the wiring of the X electrodes 201 and the wiring of the Y electrodes 202 are respectively connected to terminals 301 and 302. The terminals 301 and 302 are connected to the driver circuit 102 (see FIG. 1).

The shape of the X electrodes 201 and the Y electrodes 202 is quadrilateral (rhombus or rectangle), for example. The X electrodes 201 are linked to each other in a beaded configuration in the x direction via bridge electrodes 311X (see FIG. 2(B)) that are first connection units. That is, the X electrodes 201 are arrayed in the x direction. X electrodes that are electrically connected in the x direction in this manner are referred to as an X electrode group. The X electrode groups, each of which has the X electrodes linked in a beaded configuration in the x direction, are disposed at 2 mm intervals in the y direction, for example. The X electrode groups extend in parallel with each other in the y direction.

The Y electrodes 202 are linked to each other in a beaded configuration in the y direction via bridge electrodes 311Y (see FIG. 2(B)) that are second connection units. That is, the Y electrodes 202 are arrayed in the y direction. Y electrodes that are electrically connected in the y direction in this manner are referred to as a Y electrode group. The Y electrode groups, each of which has the Y electrodes linked in a beaded configuration in the y direction, are disposed at 2 mm intervals in the x direction, for example. The Y electrode groups extend in parallel with each other in the x direction.

The X electrode groups and the Y electrode groups are formed such that the first connection units (bridge electrodes 311X) and the second connection units (bridge electrodes 311Y) overlap each other via the insulating film 203 in a plan view. As shown in FIG. 2(C), the bridge electrodes 311X and the bridge electrodes 311Y are insulated from each other by the insulating film 203. In other words, the X electrode groups and the Y electrode groups are formed so as to cross each other in different planes with the insulating film 203 therebetween. Also, the X electrodes 201 and the Y electrodes 202 are formed so as not to overlap each other in a plan view. That is, the X electrodes 201 and the Y electrodes 202 are formed so as to be adjacent to each other in a plan view.

Next, the manufacturing method will be explained with reference to the view (C) in FIG. 2. The support substrate 310 is a transparent insulating substrate such as a glass substrate, for example. First, the bridge electrodes 311X are formed using a transparent conductive film such as ITO on a first surface 310a of the support substrate 310. Next, the insulating film 203 on the bridge electrodes 311X is formed using SiN (silicon nitride film) or the like.

The insulating film 203 is formed to cover the bridge electrodes 311X so as to insulate the bridge electrodes 311X from the Y electrodes 202 and the bridge electrodes 311Y, while leaving a portion of the bridge electrodes 311X uncovered to allow contact between the bridge electrodes 311X and the X electrodes 201. Next, the X electrodes 201, the Y electrodes 202, the bridge electrodes 311Y, the wiring, and the terminals 301 and 302 are simultaneously formed by the transparent conductive film. Lastly, an insulating film 312 is formed of SiN (silicon nitride film) or the like and contact holes are formed therein at the terminals 301 and 302.

By applying a voltage to the terminals 301 and 302 of the electrode substrate 101 configured as described above, an electric field is generated between the X electrode groups and the Y electrode groups. If the intensity of the generated electric field exceeds the dielectric breakdown level of air, then ozone is generated by electric discharge. Positions on the insulating film 312 where ozone is generated include the space in the single electrode layer between the X electrodes 201 and the Y electrodes 202 such as that indicated by the region 321, or the space between multiple electrode layers, or in other words, between the bridge electrodes 311X and the bridge electrodes 311Y via the insulating film 203 such as that indicated by the region 322.

Figure 3A:
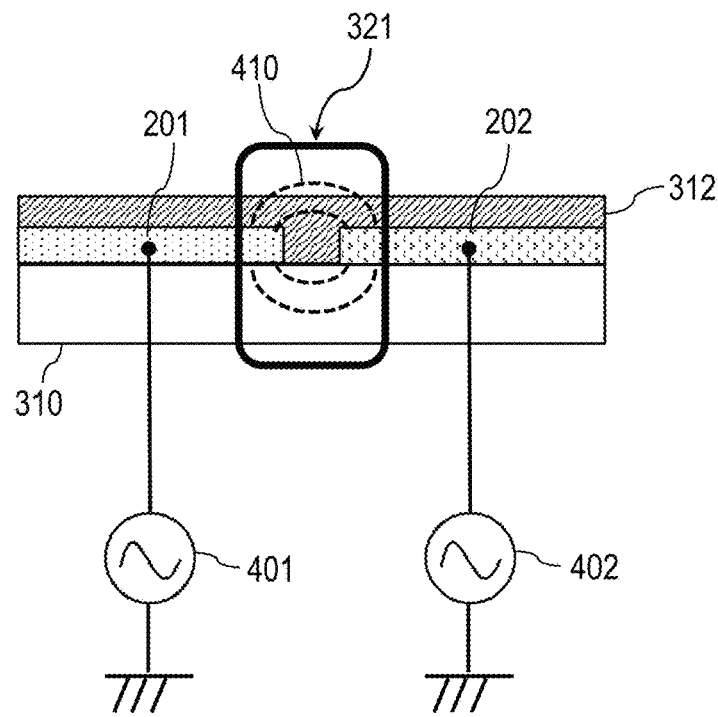
FIGS. 3A and 3B are descriptive drawings showing the manner in which ozone is generated.
Figure 3B:
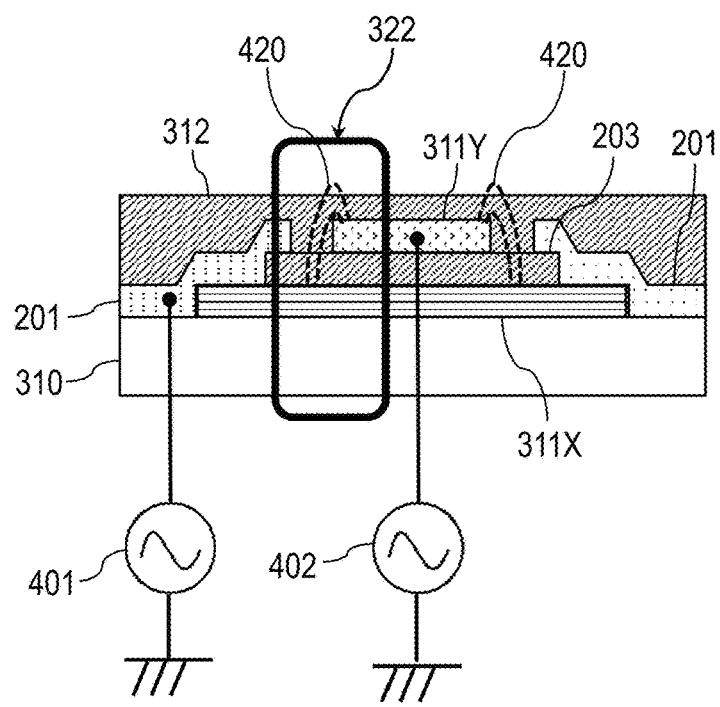

FIGS. 3A and 3B are a descriptive drawing showing the manner in which ozone is generated. FIG. 3A illustrates the manner in which ozone is generated in an electric field generation region 321 in the space within the single electrode layer shown in (B) in FIG. 2, and FIG. 3B illustrates the manner in which ozone is generated in the electric field generation region 322 in the space between multiple electrode layers shown in (C) in FIG. 2. A signal power source 401 is an alternating current power source that applies a voltage to the X electrodes 201, and a signal power source 402 is an alternating current power source that applies a voltage to the Y electrodes 202.

In one example, the output of the signal power source 401 is set to GND, and the output of the signal power source 402 is set to a prescribed alternating current voltage. In this case, an electric field 410 is generated in the space within the single electrode layer of FIG. 3A due to the potential difference between the X electrode 201 and the Y electrode 202, and an electric field 420 is generated in the space between multiple electrode layers of FIG. 3B due to the potential difference between the bridge electrode 311X and the bridge electrode 311Y. When the intensity of the electric fields 410 and 420 in the air above the insulating film 312 reaches a prescribed value, dielectric breakdown occurs in the air. When dielectric breakdown occurs in the air, this results in silent discharge and the generation of ozone.

Figure 4:
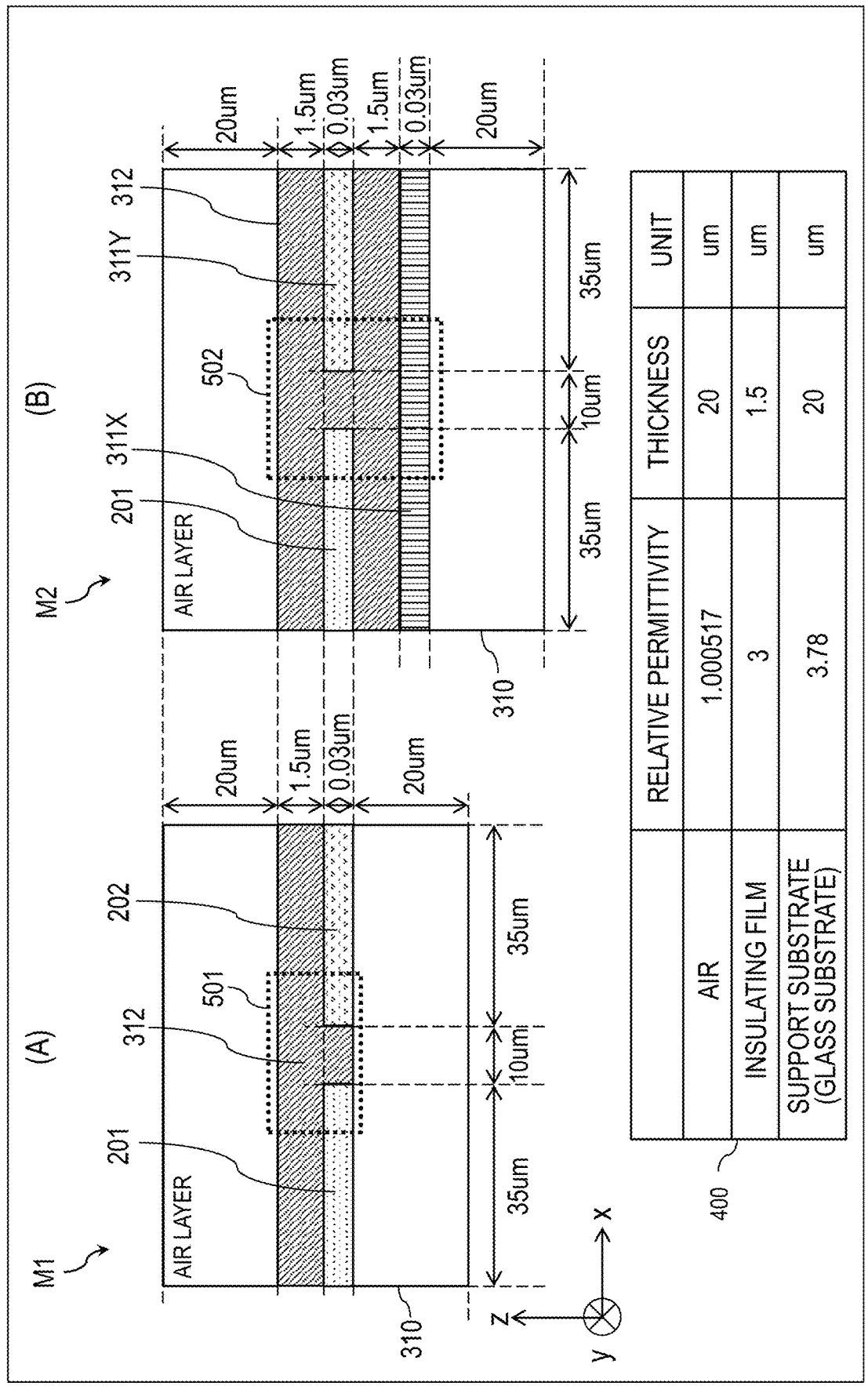
FIG. 4 is a descriptive view a model that simulates the electric field generated when a voltage is applied to the electrode substrate.

FIG. 4 is a descriptive view a model that simulates the electric field generated when a voltage is applied to the electrode substrate 101. The model of FIG. 4 is a 3-dimensional model that simplifies that multilayer structure of the electrode substrate 101 for which the manner in which ozone is generated was shown in FIG. 3. In FIG. 4, the z direction is a direction perpendicular to the plane of the electrode substrate 101, the x direction is the direction in which the X electrodes 201 and the bridge electrodes 311X are connected, and the y direction is the direction in which the Y electrodes 202 and the bridge electrodes 311Y are connected.

In FIG. 4, the left side drawing illustrates the xz cross-section of a 3-dimensional simulation model of the electric field generation region 321 in the space within the single electrode layer. That is, the left side drawing in FIG. 4 illustrates a 3-dimensional model in which the 3-dimensional region encompassing the electric field generation region 321 of FIG. 3A is simplified. In FIG. 4, the right side drawing illustrates the xz cross-section of a 3-dimensional simulation model of the electric field generation region 322 in the space between multiple electrode layers. That is, the right side drawing in FIG. 4 illustrates a 3-dimensional model in which the 3-dimensional region encompassing the electric field generation region 322 of FIG. 3B is simplified. The 3-dimensional simulation model of the electric field generation region 321 in the space within the single electrode layer is referred to as a single layer electrode model M1, and the 3-dimensional simulation model of the electric field generation region 322 in the space between multiple electrode layers is referred to as a multilayer electrode model M2.

The relative permittivity, the thickness, and the unit for the air, the insulating film 312, and the support substrate 310 are as shown in the table 400 for both the single layer electrode model M1 and the multilayer electrode model M2. The thicknesses of the X electrodes 201, the Y electrodes 202, and the insulating film 312 are as shown in FIG. 4. The gap between the X electrodes 201 and the Y electrodes 202 in the single layer electrode model M1 and the gap between the X electrodes 201 and the bridge electrodes 311Y of the multilayer electrode model M2 were both set to 10 μm, and the width of each electrode was set to 35 μm for ease of calculation. Although not shown, the single layer electrode model M1 and the multilayer electrode model M2 are 3-dimensional models having a depth in the y direction.

The applied voltage to the X electrodes 201 and the bridge electrodes 311X is V1 and the applied voltage to the Y electrodes 202 and the bridge electrodes 311Y is V2. A simulation of the intensity of the electric field generated within each 3-dimensional model (M1, M2) was executed, with the applied voltage V1 being set to GND and the applied voltage V2 being set to 15V, 30V, 150V, and 600V. Regarding the results, in the xz plane at the center of the y direction of each model, the electric field distribution generated at focus regions 501 and 502 centered on the electrodes that are 10 μm apart was subject to analysis.

Figure 5A:
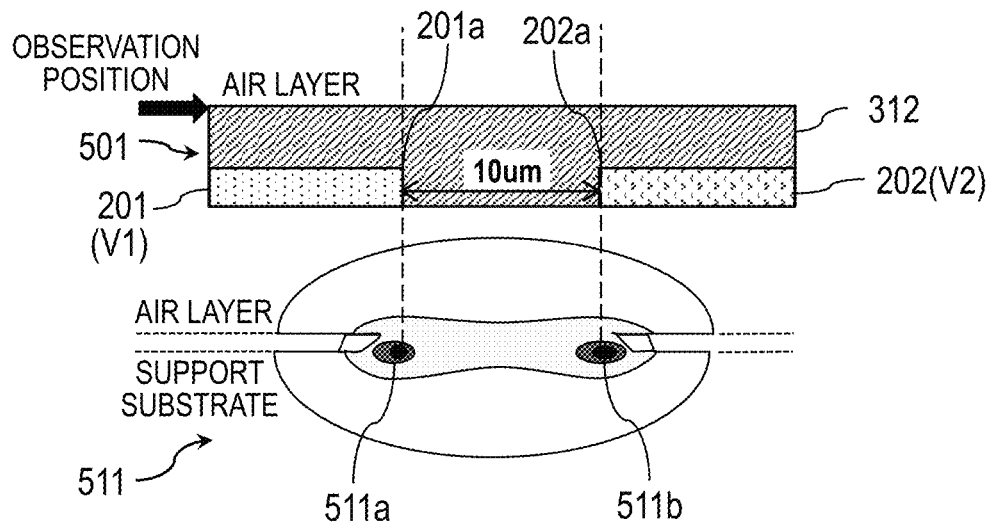
FIGS. 5A and 5B illustrate heat maps of the electric field intensity distribution in the focus regions.
Figure 5B:
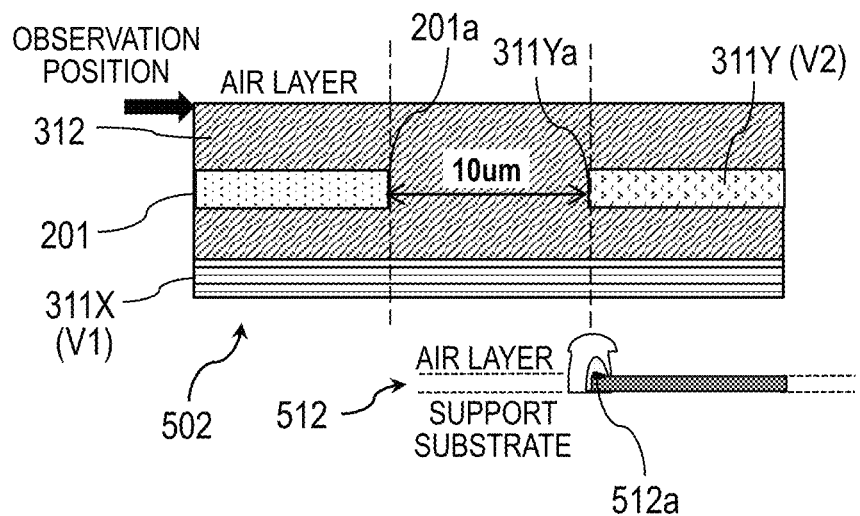

FIGS. 5A and 5B illustrate heat maps of the electric field intensity distribution in the focus regions. The heat maps 511 and 512 are data that illustrates an overhead visualization of the electric field intensity distribution according to whether the voltage V2 is 15V, 30V, 150V, or 600V (V2=15V, for example), and the heat maps indicate the electric field intensity within the focus regions 501 and 502.

In the heat maps 511 and 512, the electric field intensity is represented in grayscale, and the darker the color is, the more intense the electric field is. Within the focus region 501 shown in FIG. 5A, the electric field intensity is greater between the X electrode 201 and the Y electrode 202 and in areas close to opposing ends 201a and 202a of the X electrode 201 and the Y electrode 202, and the peak values (maximum values) 511a and 511b for the electric field intensity are attained at the ends 201a and 202a.

Meanwhile, within the focus region 502 shown in FIG. 5B, the electric field intensity is greater towards an end 311Ya of the bridge electrode 311Y opposing the X electrode 201, and the peak value (maximum value) 512a for the electric field intensity is attained at the end 311Ya. Also, as can be seen in the heat maps 511 and 512, the electric field intensity of the air layer decreases, moving away from the support substrate 310.

Figure 6A:
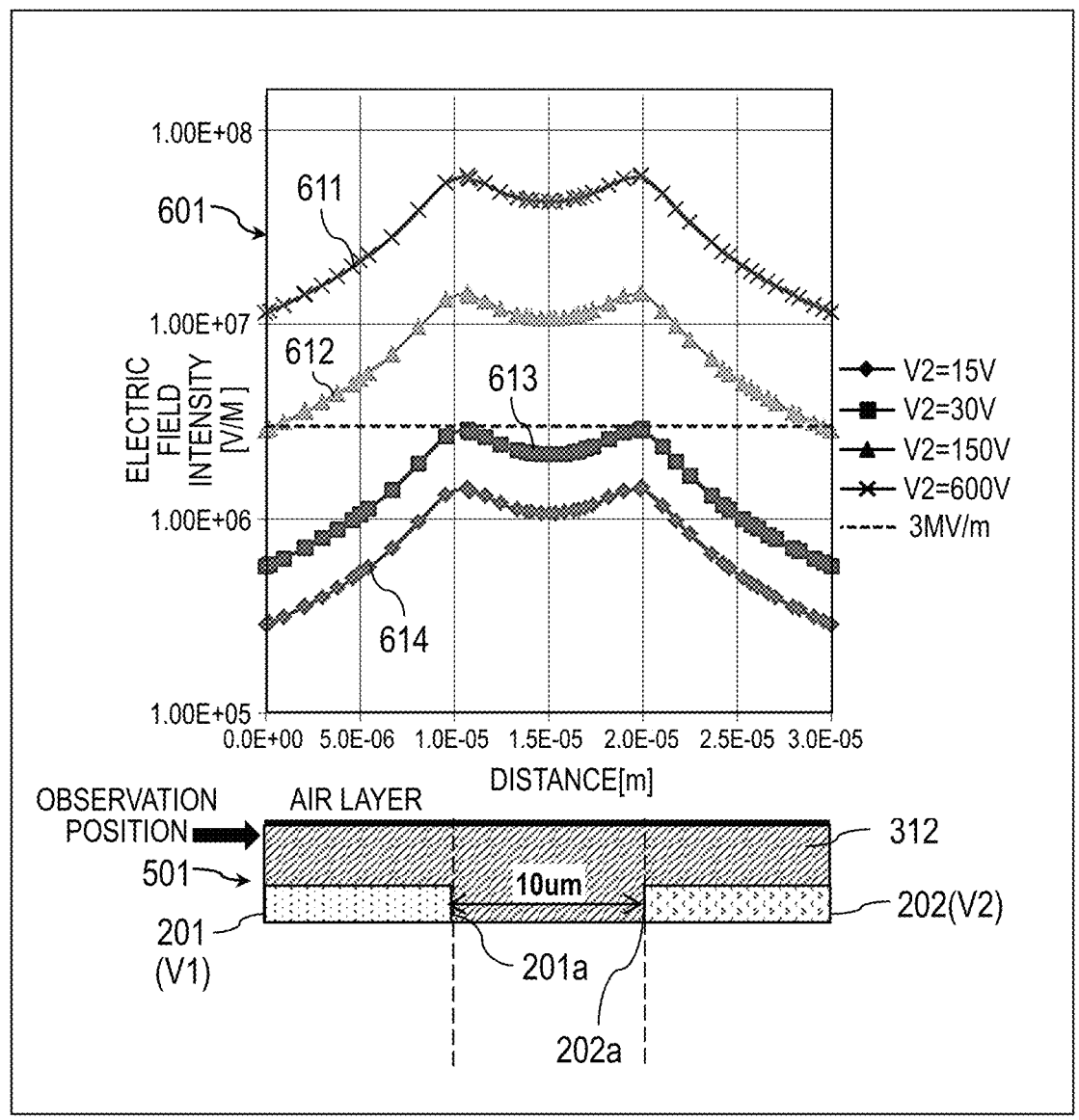
FIGS. 6A and 6B are descriptive views of a result 1 of analyzing the electric field intensity in the vicinity of an observed position according to the simulation results of FIG. 4.
Figure 6B:
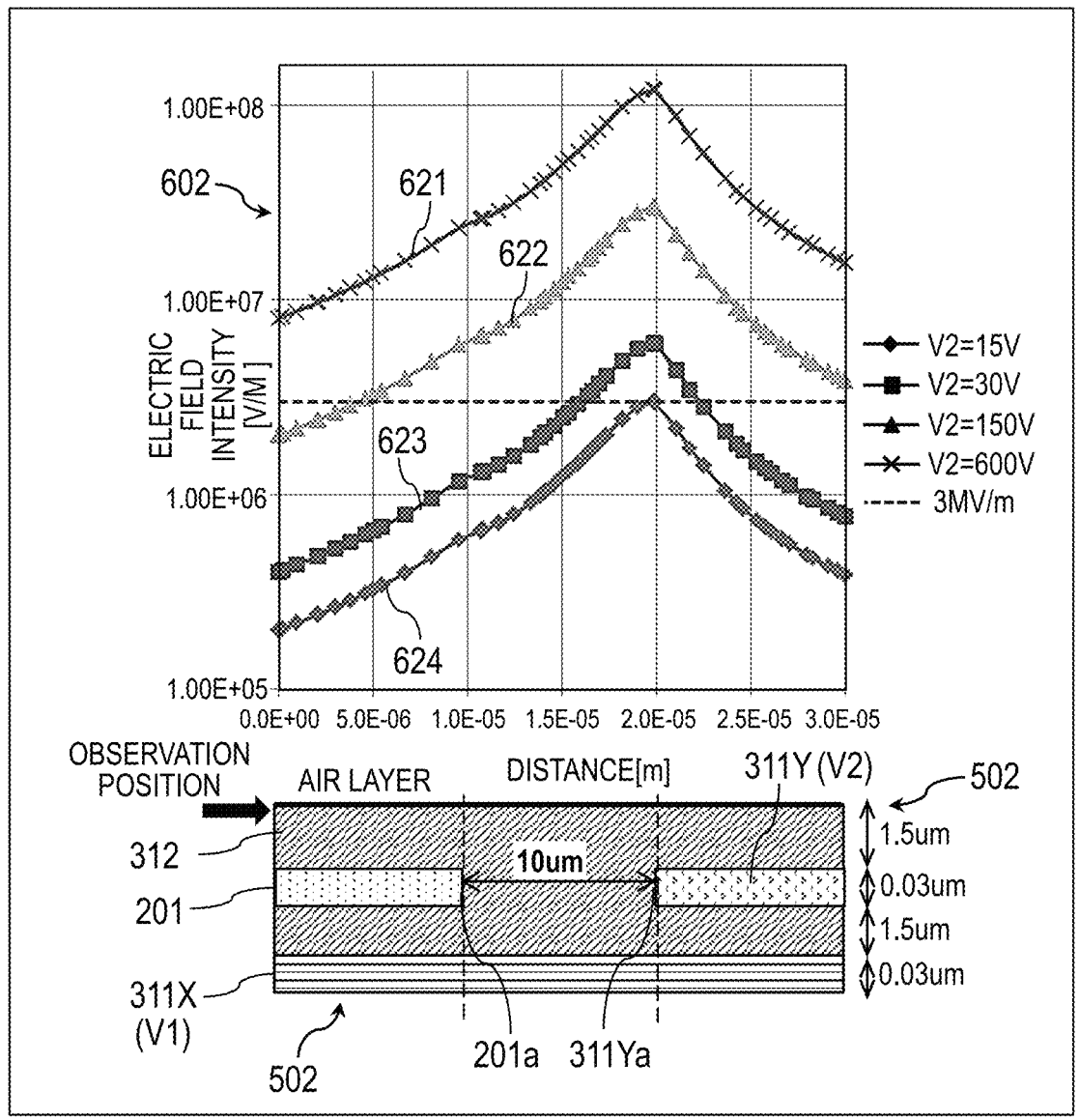

FIGS. 6A and 6B are descriptive views of a result 1 of analyzing the electric field intensity in the vicinity of an observed position according to the simulation results of FIG. 4. FIG. 6 does not show an overhead view of an electric field intensity distribution as in FIGS. 5A and 5B, but rather illustrates the electric field intensity distribution for when the applied voltage V2 is 600V between the Y electrode 202 and the bridge electrode 311Y, and the boundary between the air and the insulating film 312 is the observed position.

FIG. 6A illustrates the result 1 of the single layer electrode model M1 (in the focus region 501), and FIG. 6B illustrates the result 1 of the multilayer electrode model M2 (in the focus region 502). The graphs 601 and 602 show the dependence on the voltage V2 of the electric field intensity of the air layer at the boundary with the insulating film 312. The vertical axes of the graphs 601 and 602 indicate the electric field intensity (MV/m) of the air layer at the boundary with the insulating film 312. The horizontal axis indicates the x direction positions corresponding to the focus regions 501 and 502, and the horizontal axis coordinate of 1.5E-05 is the center position in the x direction of the models M1 and M2.

In other words, in FIG. 6A, the horizontal axis coordinate of 1.0E-05 corresponds to the position of the end 201a of the X electrode 201, the horizontal axis coordinate of 2.0E-05 corresponds to the position of the end 202a of the Y electrode 202, and the gap therebetween is 10 μm (similarly applies to FIGS. 7A,7B and 8A,8B. Similarly, in FIG. 6B, the horizontal axis coordinate of 1.0E-05 corresponds to the position of the end 201a of the X electrode 201, the horizontal axis coordinate of 2.0E-05 corresponds to the position of the end 311Ya of the bridge electrode 311Y, and the gap therebetween is 10 μm (similarly applies to FIGS. 7A, 7B and 8A, 8B.

The dotted lines of the graphs 601 and 602 indicate the electric field intensity (3MV/m) at which the air undergoes dielectric breakdown. When the electric field intensity is 3MV/m or greater, ozone is generated on the electrode substrate 101. As shown in graphs 601 and 602, the greater the applied voltage V2 on the Y electrode 202 and the bridge electrode 311Y is, the higher the electric field intensity is. According to the graphs 601 and 602, where V2 is 600V, the electric field intensity in the air layer at the boundary with the insulating film 312 is sufficiently higher than 3MV/m, and it can be understood that ozone is generated as a result.

Figure 7A:
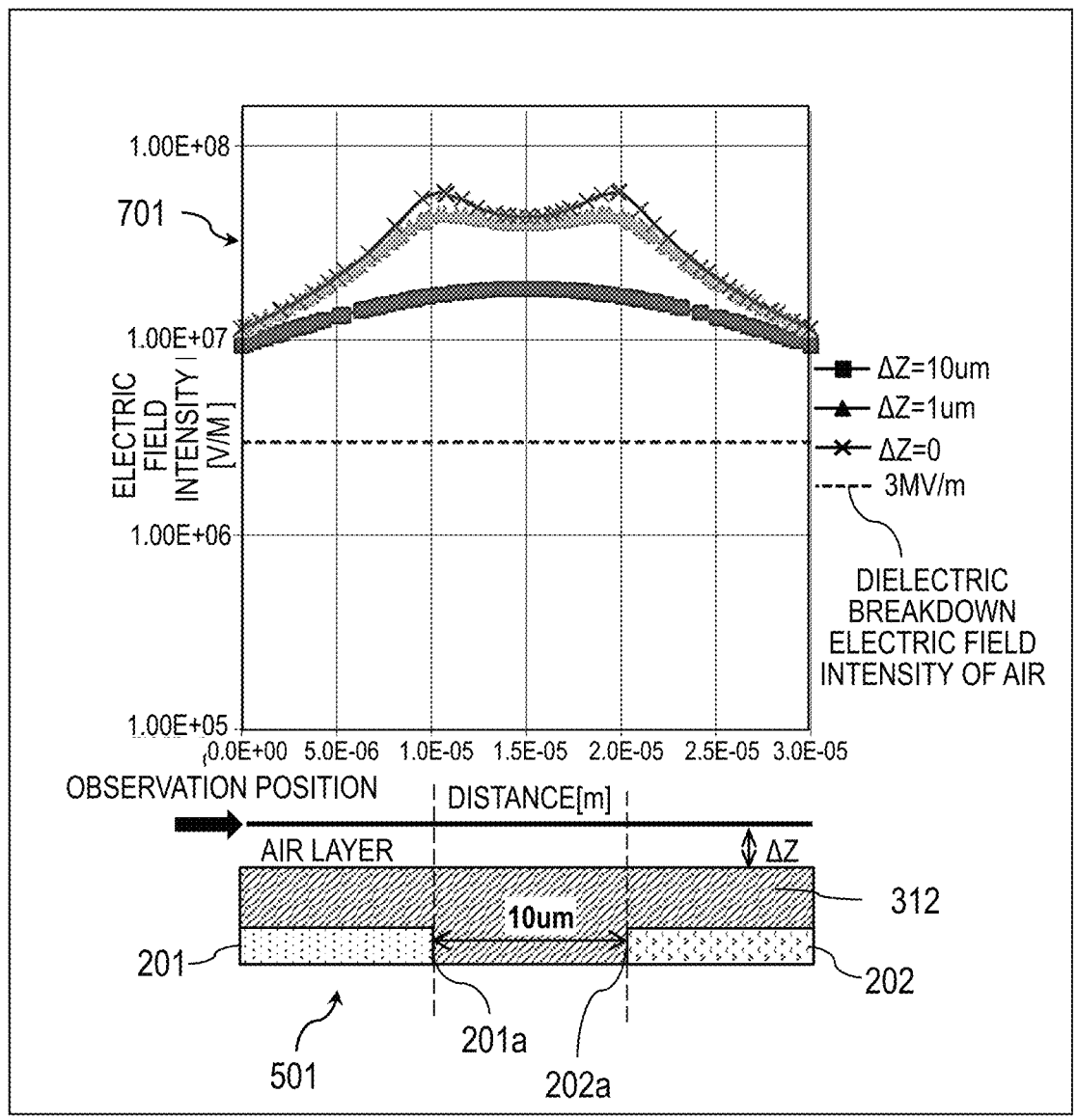
FIGS. 7A and 7B are descriptive views showing a result 2 of analyzing the electric field intensity in the vicinity of an observed position according to the simulation results of FIG. 4.
Figure 7B:
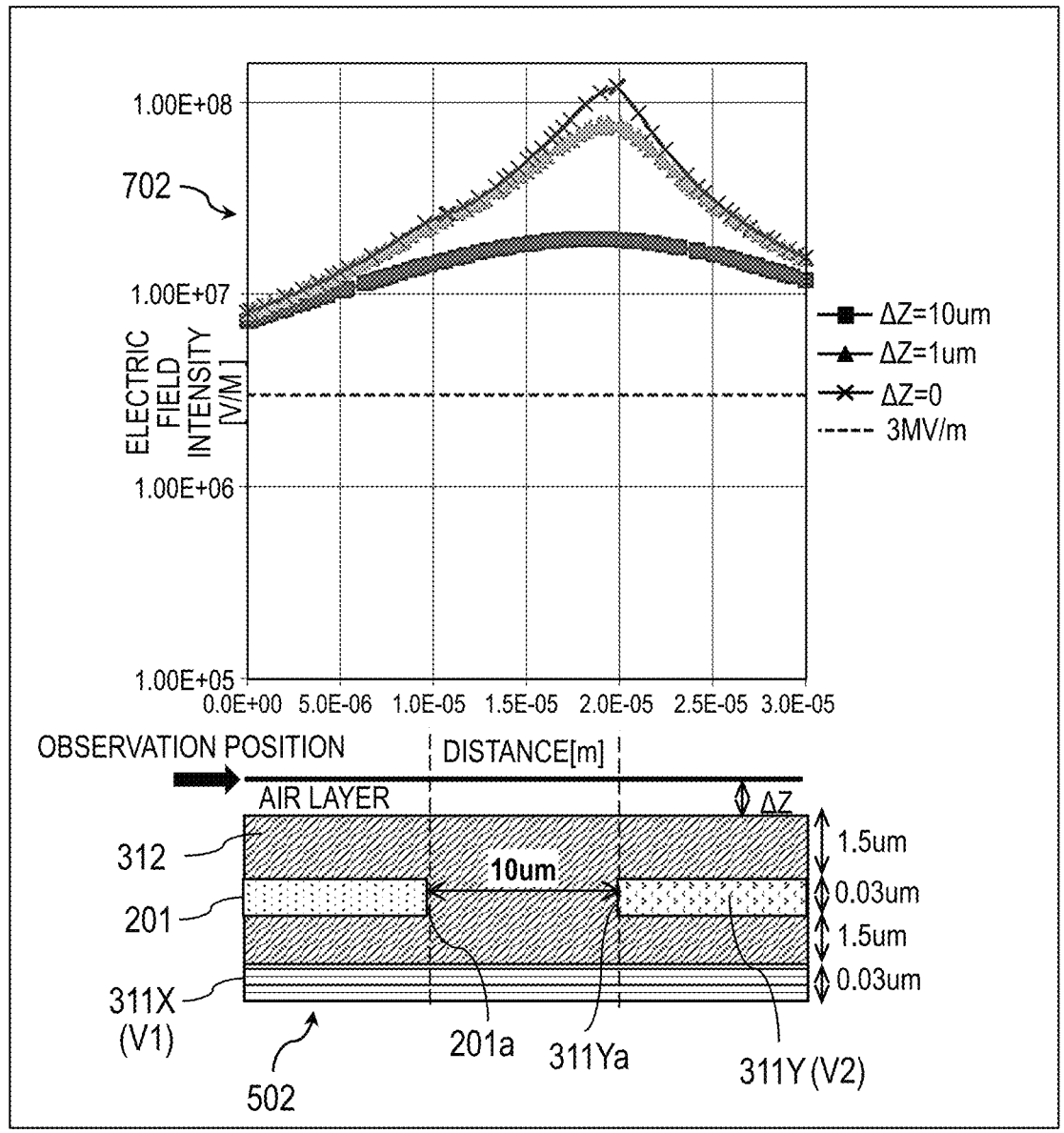

FIGS. 7A and B are descriptive views showing a result 2 of analyzing the electric field intensity in the vicinity of an observed position according to the simulation results of FIG. 4. FIG. 7s. 7A and B illustrate the electric field intensity distribution of the air layer for when the applied voltage V2 is 600V between the Y electrode 202 and the bridge electrode 311Y, and the position of the air layer at a distance ΔZ from the boundary with the insulating film 312 is the observed position. FIG. 7A illustrates the result 2 of the single layer electrode model M1 (in the focus region 501), and FIG. 7B illustrates the result 2 of the multilayer electrode model M2 (in the focus region 502).

The graphs 701 and 702 show the dependence of the electric field intensity of the air layer on the distance ΔZ (observed position) from the boundary with the insulating film 312. The vertical axis indicates the electric field intensity (MV/m), the horizontal axis, similar to the graphs 601 and 602, indicates the x direction positions corresponding to the focus regions 501 and 502, and the horizontal axis coordinate of 1.5E-5 is the center position in the x direction of the models M1 and M2. The dotted lines indicate the electric field intensity (3MV/m) at which the air undergoes dielectric breakdown. When the electric field intensity is 3MV/m or greater, ozone is generated on the electrode substrate 101.

As can be seen in graphs 701 and 702, in both the single layer electrode model M1 and the multilayer electrode model M2, the electric field intensity of the air layer is lower in areas farther away from the boundary with the insulating film 312, but even when ΔZ is 10 μm, the electric field intensity sufficiently exceeds 3MV/m. This indicates that it is possible to generate ozone on the electrode substrate 101.

Figure 8A:
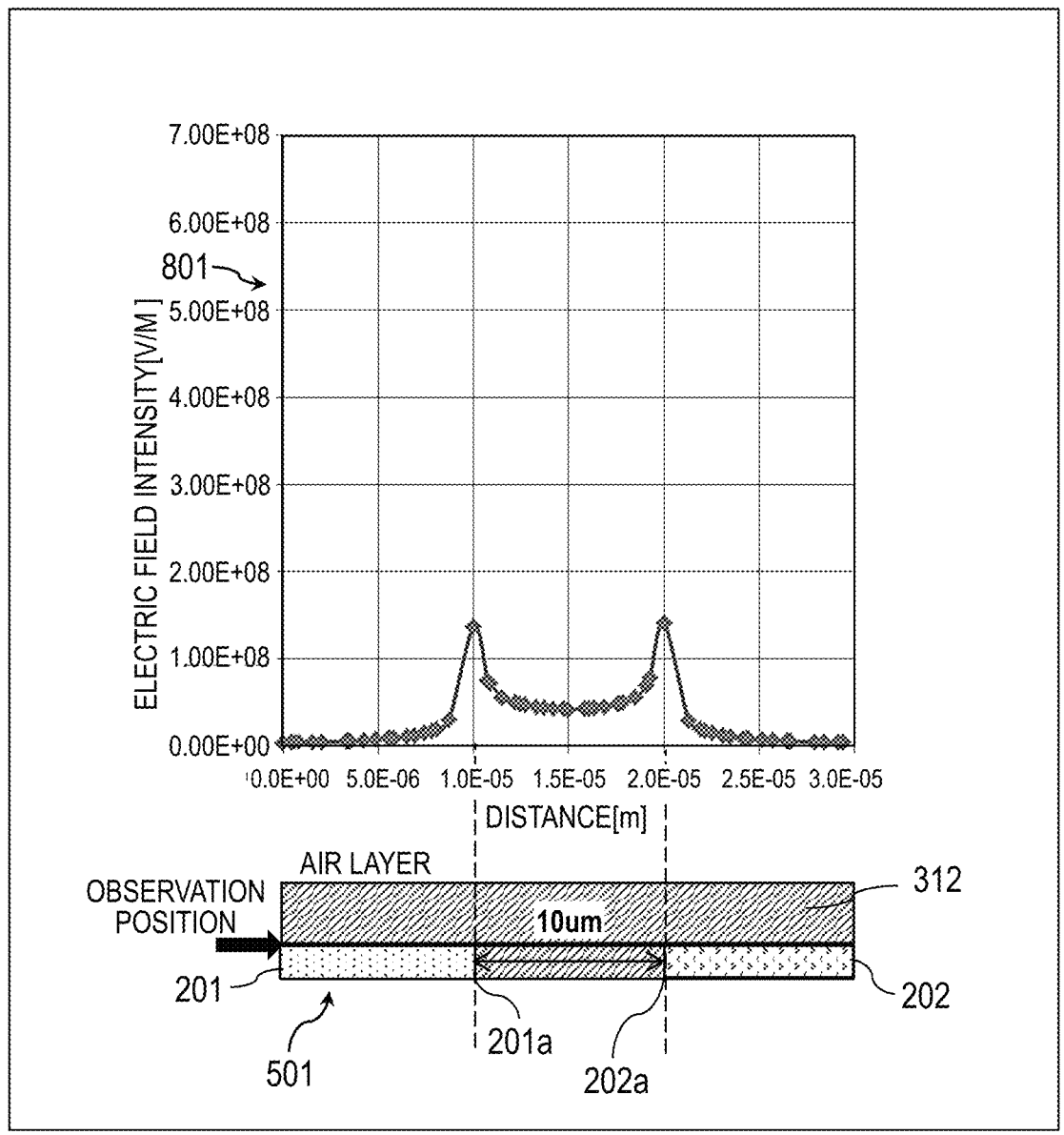
FIGS. 8A and 8B are descriptive views showing a result 3 of analyzing the electric field intensity in the vicinity of an observed position according to the simulation results of FIG. 4.
Figure 8B:
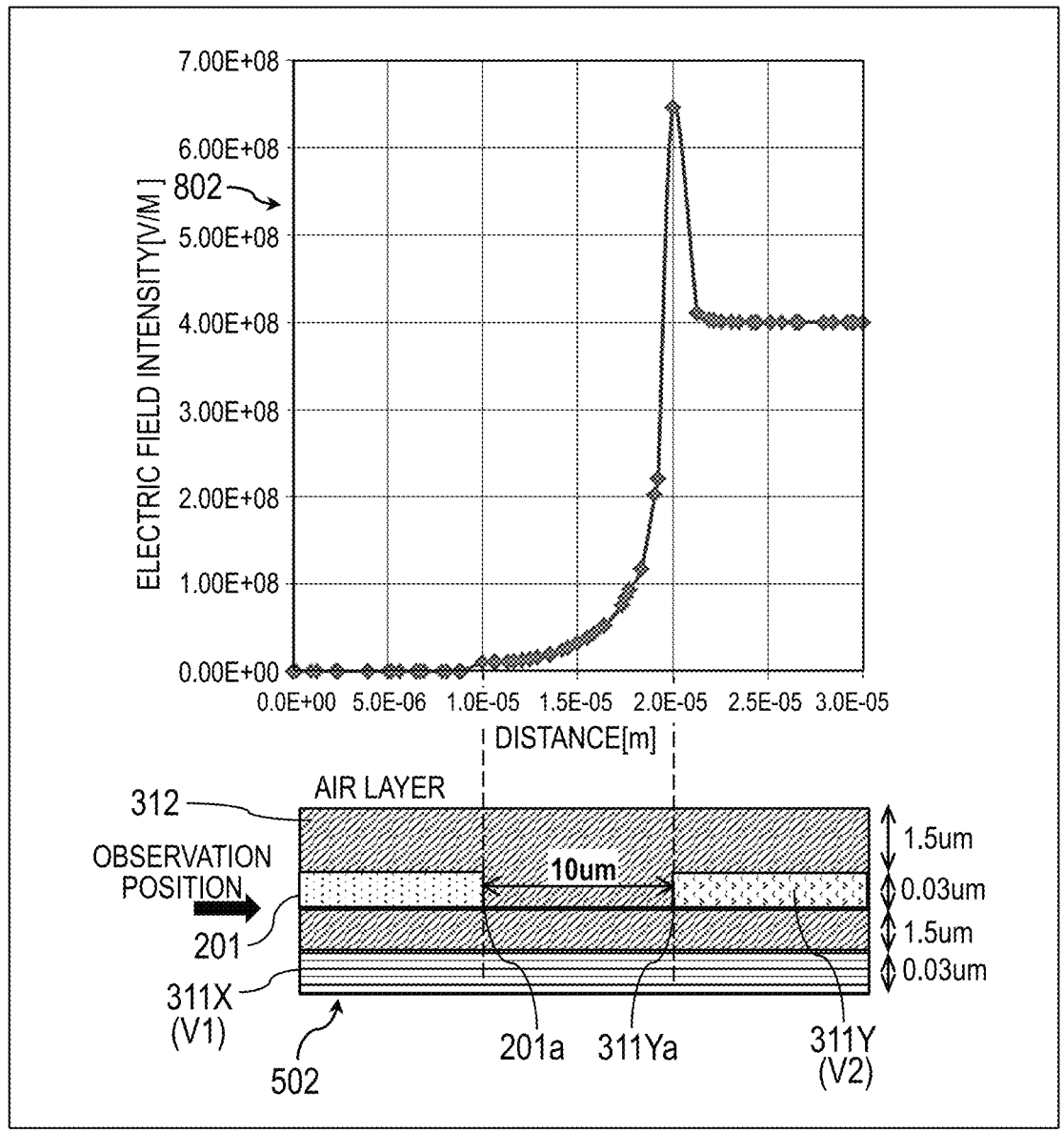

FIGS. 8A and 8B are descriptive views showing a result 3 of analyzing the electric field intensity in the vicinity of an observed position according to the simulation results of FIG. 4. FIGS. 8A and 8B illustrate the electric field intensity distribution within the insulating film 312 for when the applied voltage V2 is 600V between the Y electrode 202 and the bridge electrode 311Y.

FIG. 8A illustrates the result 3 of the single layer electrode model M1 (in the focus region 501), and FIG. 8B illustrates the result 3 of the multilayer electrode model M2 (in the focus region 502). The observed position of FIG. 8A is the boundary between the insulating film 312 and the X electrode 201 and Y electrode 202, and the observed position of FIG. 8B is the boundary between the insulating film 312 and the surface of the X electrode 201 and the bridge electrode 311Y facing the bridge electrode 311X.

The graphs 801 and 802 indicate the electric field intensity distribution in the insulating film 312 at the observed position. The vertical axis indicates the electric field intensity (MV/m), the horizontal axis indicates the positions corresponding to the focus regions 501 and 502 in the x direction, and the horizontal axis coordinate of 1.5E-05 is the center position in the x direction of the models M1 and M2.

In this simulation, the electric field intensity in the single layer electrode model M1 (in the focus region 501) is determined according to the gap between the X electrode 201 and the Y electrode 202, and by the value of V2-V1. Also, the electric field intensity in the multilayer electrode model M2 (in the focus region 502) is determined according to the thickness of the insulating film 312 between the bridge electrodes 311X and 311Y, and by the value of V2-V1.

As can be seen in graphs 801 and 802, the electric field intensity in the insulating film 312 is greater in the multilayer electrode model M2 than in the single layer electrode model M1. The electric field intensity in the multilayer electrode model M2 is less than 700MV/m under the conditions of this simulation (|V2-V1|=600V, insulating film thickness=0.03 μm). Thus, if SiN (silicon nitride film), for which the dielectric breakdown electric field intensity is 800MV/m, is used for the insulating film 312, for example, then no dielectric breakdown occurs, and it is possible to generate ozone. Furthermore, it is possible to use an insulating film with an even higher dielectric breakdown electric field intensity, and it is possible to use $SiO_2$ (silicon oxide film) or a layered structure of SiN and $SiO_2$, for example.

Figure 9:
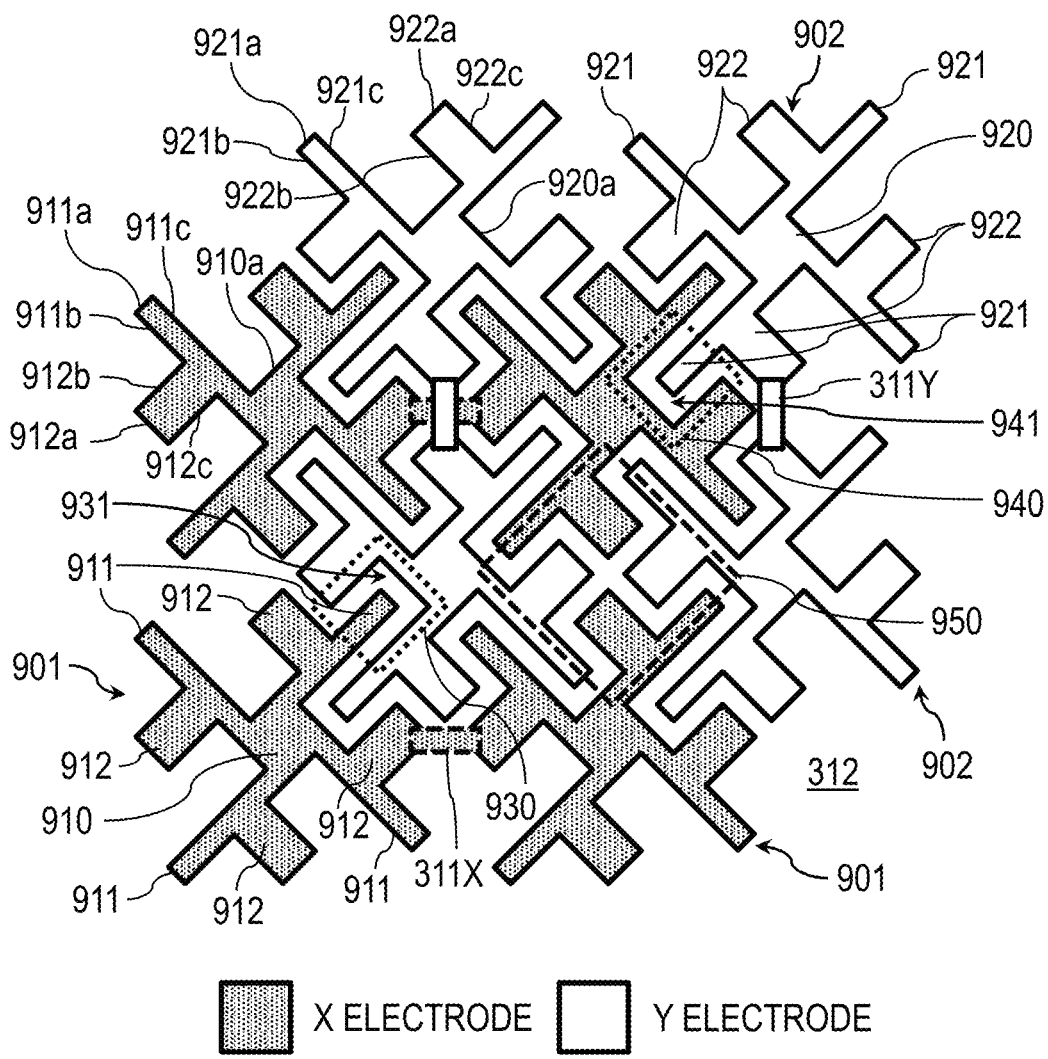
FIG. 9 is a descriptive drawing showing a modification example of the electrode shape.

FIG. 9 is a descriptive drawing showing a modification example of the electrode shape. The X electrodes 901 and the Y electrodes 902 of the present modification example have a shape with more vertices and sides than the quadrilaterals shown in (A) in FIG. 2. Specifically, for example, the X electrodes 901 have a rectangular center section 910, four first projections 911 that protrude from the center section 910 along the sides of the center section 910, and four second projections 912 that protrude from intermediate parts of the first projections 911 in directions perpendicular to the protruding directions of the first projections 911. The Y electrodes 902 similarly have a rectangular center section 920, four third projections 921 that protrude from the center section 920 along the sides of the center section 920, and four fourth projections 922 that protrude from intermediate parts of the third projections 921 in directions perpendicular to the protruding directions of the third projections 921.

The X electrode 901 has a region 940 where the X electrode 901 and the Y electrode 902 are adjacent to each other, the region 940 having a recess 941 formed by a side 910a of the center section 910, a side 911c of the first projection 911 that is perpendicular to the side 910a, and a side 912c of the second projection 912 that opposes the side 911c, for example. The third projection 921 of the Y electrode 902 is disposed in the recess 941. The sides 921a to 921c of the third projection 921 oppose the sides 910a, 911c, and 912c forming the recess 941, and thus, compared to a quadrilateral X electrode 201, the area of the electric field generation region 321 in the space within the single electrode layer is increased.

The Y electrode 902 similarly has a region 930 where the X electrode 901 and the Y electrode 902 are adjacent to each other, the region 930 having a recess 931 formed by a side 920a of the center section 920, a side 921c of the third projection 921 that is perpendicular to the side 920a, and a side 922b of the fourth projection 922 that opposes the side 921c, for example. The first projection 911 of the X electrode 901 is disposed in the recess 931. The sides 911a to 911c of the first projection 911 oppose the sides 920a, 921c, and 922b forming the recess 931, and thus, compared to a quadrilateral Y electrode 202, the area of the electric field generation region 321 in the space within the single electrode layer is increased.

Also, in the region 950 where two X electrodes 901 are adjacent to two Y electrodes 902, for example, each of the X electrodes 901 is arranged such that a tip side 912a of the second projection 912 of the X electrode 901 opposes a lateral side 922c of the fourth projection 922 of one Y electrode 902, the lateral side 912c opposes the lateral side 921b of the third projection 921 of the one Y electrode 902, and the lateral side 912b opposes a tip side 922a of the fourth projection 922 of the other Y electrode 902. Thus, compared to a quadrilateral X electrode 201, the area of the electric field generation region 321 in the space within the single electrode layer is increased.

Similarly, in the region 950, each of the Y electrodes 902 is arranged such that the tip side 922a of the fourth projection 922 of the Y electrode 902 opposes a lateral side 912b of the second projection 912 of one X electrode 901, the lateral side 922b opposes the lateral side 911b of the first projection 911 of the one X electrode 901, and the lateral side 922c opposes the tip side 912a of the second projection 912 of the other X electrode 901. Thus, compared to a quadrilateral Y electrode 202, the area of the electric field generation region 321 in the space within the single electrode layer is increased. Thus, in the regions 930, 940, and 950, the area of the electric field generation region 321 in the space within the single electrode layer is increased, enabling an increase in the ozone generation region.

Also, the electrode shape is not limited to the shapes depicted in FIGS. 2 and 9, and may be yet another shape. In the single layer electrode structure, if the distance between two electrodes is reduced, the generated electric field intensity is increased, enabling a decrease in the voltage necessary to generate ozone. That is, it is possible to reduce power consumption. However, in a single layer electrode structure, if the distance between electrodes is reduced, a high degree of machining precision would be required in order to prevent shorting between electrodes in the same layer. Thus, a multilayer electrode structure such as that of the region 322, for example, is preferable for reducing power consumption due to the ease of machining thereof.

Figure 10A:
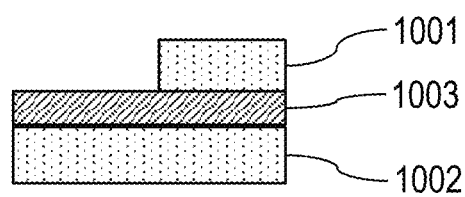
FIGS. 10A and 10B are conceptual drawings indicating a multilayer electrode structure.
Figure 10B:
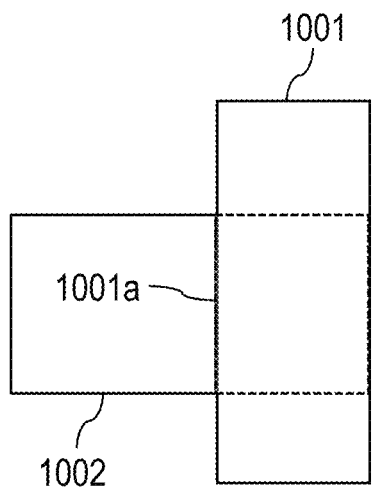

FIGS. 10A and 10B are conceptual drawings indicating a multilayer electrode structure; FIG. 10A is a cross-sectional view of the multilayer electrode structure, and FIG. 10B is a plan view of the multilayer electrode structure. Electrodes 1001 and 1002 that generate ozone oppose each other via an insulating film 1003. In the plan view of FIG. 10B, an edge 1001a of the electrode 1001 is present within the region of the electrode 1002. That is, a multilayer electrode structure suitable for generating ozone is not limited to the region 322 of FIG. 3, and is a structure in which the two electrodes 1001 and 1002 are layered with the insulating film 1003 therebetween, and the edge 1001a of one electrode 1001 is present in the region of the other electrode 1002 in a plan view.

According to Embodiment 1, the driver circuit 102 applies the voltages V1 and V2 to the X electrodes 201 and the Y electrodes 202 (or the bridge electrodes 311X and the bridge electrodes 311Y) such that the intensity of the electric field generated when the voltage is applied to the electrode substrate 101 is greater than or equal to the dielectric breakdown electric field intensity of air but less than the dielectric breakdown electric field intensity of the silicon nitride (SiN) film. As a result, it is possible to generate ozone on the surface 101a of the electrode substrate 101 without damaging the insulating film 312. Also, by changing the electrode shape to that of FIG. 9, the ozone generation region is expanded, and thus, it is possible to shorten the time required for the disinfection process on the surface 101a of the electrode substrate 101.

Additionally, according to the electronic apparatus 100A of Embodiment 1, the X electrodes 201 and the Y electrodes 202 that cause ozone to be generated are present only on the first surface 310a, which is one side of the support substrate 310. Thus, it is possible to disinfect the surface 101a of the electrode substrate 101. Also, the first surface 310a opposes the display surface of the display medium 104 on which images are displayed. Thus, in the electronic apparatus 100A, images can be viewed from the electrode substrate 100A, and it is possible to disinfect the display surface of the display medium 104 opposing the surface 101a of the electrode substrate 101.

Embodiment 2

Next, Embodiment 2 will be described. Embodiment 2 has a configuration in which a human detection sensor is connected to the control circuit 103 of Embodiment 1. In Embodiment 2, the same components as those of Embodiment 1 are assigned the same reference characters and descriptions thereof are omitted.

Figure 11:
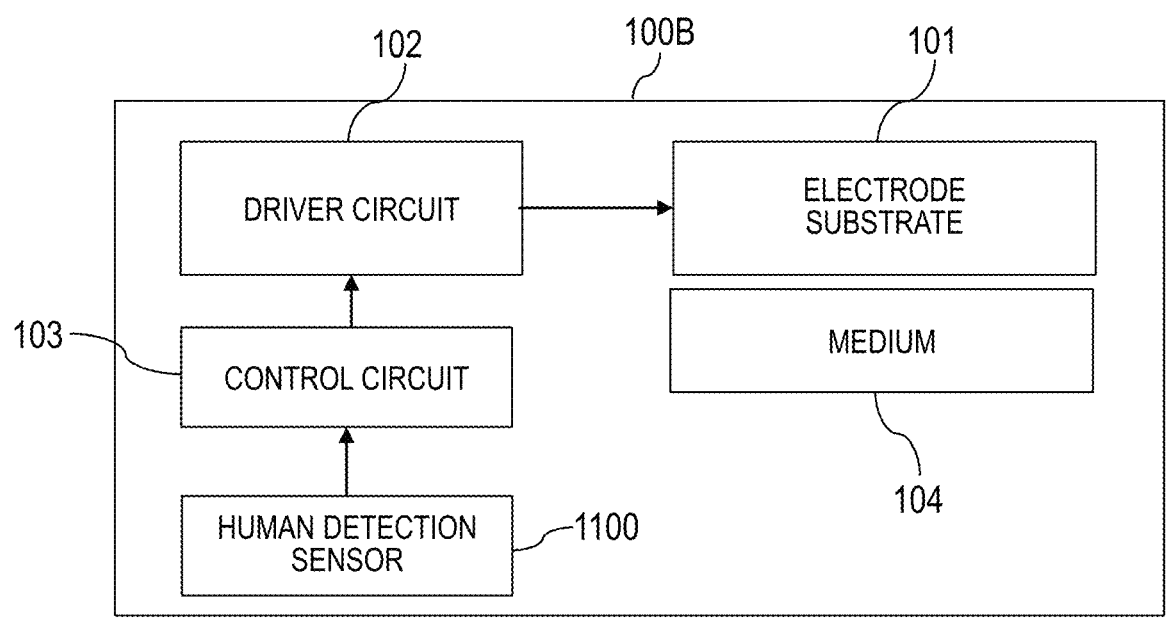
FIG. 11 is a block diagram showing a configuration example of an electronic apparatus according to Embodiment 2.

FIG. 11 is a block diagram showing a configuration example of an electronic apparatus 100B according to Embodiment 2. The electronic apparatus 100B has a human detection sensor 1100. The human detection sensor 1100 is connected to the control circuit 103. The human detection sensor 1100 is a sensor that detects a living body, and thus, an infrared sensor can be used therefor. The infrared sensor detects infrared beams emitted from a living body in the vicinity of the electrode substrate 101 and outputs a detection signal to the control circuit 103.

The control circuit 103 controls the driver circuit 102 on the basis of the detection signal from the human detection sensor 1100. Specifically, for example, the control circuit 103 applies a voltage to the X electrodes 201 and the Y electrodes 202 so as to generate ozone if there is no detection signal from the human detection sensor 1100. On the other hand, the control circuit 103 does not apply a voltage to the X electrodes 201 and the Y electrodes 202 if there is a detection signal from the human detection sensor 1100.

In this manner, if a living body is not present in the vicinity of the electrode substrate 101 of the electronic apparatus 100B, then the human detection sensor 1100 does not output the detection signal regarding detection of a living body to the control circuit 103, and the driver circuit 102 applies the voltage to the X electrodes 201 and the Y electrodes 202 so as to generate ozone. Thus, the electronic apparatus 100B can disinfect the surface 101a of the electrode substrate 101 if a living body is not present in the vicinity of the electrode substrate 101 of the electronic apparatus 100B.

On the other hand, if a living body approaches the vicinity of or comes into contact with the electrode substrate 101 of the electronic apparatus 100B, then the human detection sensor 1100 outputs the detection signal regarding detection of the living body to the control circuit 103, and the driver circuit 102 does not apply the voltage to the X electrodes 201 and the Y electrodes 202. Thus, the electronic apparatus 100B can stop generation of ozone if a living body is present in the vicinity of the electrode substrate 101 of the electronic apparatus 100B. An allowable concentration for ozone that does not affect human health is cited as being 0.1 ppm, for example ("Recommendations on Allowable Concentrations (2019)," Journal of Occupational Health 2019, Japan Society for Occupational Health). By performing control using the human detection sensor 1100 such that ozone is only generated when necessary, it is possible to generate ozone within the allowable concentration limits thereof and avoid health effects.

The driver circuit 102 has a plurality of driving conditions for the electrode substrate 101 by which the amount of ozone generated differs, and may change driving conditions according to the presence or absence of a person in the vicinity as determined by the human detection sensor 1100. For example, the driver circuit 102 changes the driving conditions for the electrode substrate 101 such that if the human detection sensor 1100 detects the presence of a person, the amount of ozone generated is reduced from the current amount, and if the human detection sensor 1100 does not detect the presence of a person, the current amount of ozone generated is increased. As a result, the apparatus is safely disinfected when a person is not present and generation of ozone is stopped when a person is present, and thus, it is possible to improve safety and the efficiency of disinfection.

Alternatively, the driver circuit 102 may change the driving conditions for the electrode substrate 101 such that if the human detection sensor 1100 detects the presence of a person, the amount of ozone generated is reduced to be less than a threshold if the current amount generated is greater than or equal to the threshold, and if the human detection sensor 1100 does not detect the presence of a person, the amount of ozone generated is increased so as to be greater than or equal to a threshold if the current amount generated is less than the threshold.

Embodiment 3

Embodiment 3 will be described next. Embodiment 3 is an example in which the electrode substrate 101 is driven as a touch sensor and an ozone source. Touch sensors are sensors that detect contact by a living body (e.g., by a finger) or an object (e.g., a touch pen). Below, a case in which contact by a living body is detected will primarily be described. In Embodiment 3, the surface of the insulating film 312 layered on the electrode substrate 101 is the contact surface of the touch sensor for contact by the living body, and is therefore referred to as the contact surface 101a. In Embodiment 3, the same components as those of Embodiments 1 and 2 are assigned the same reference characters and descriptions thereof are omitted.

Figure 12:
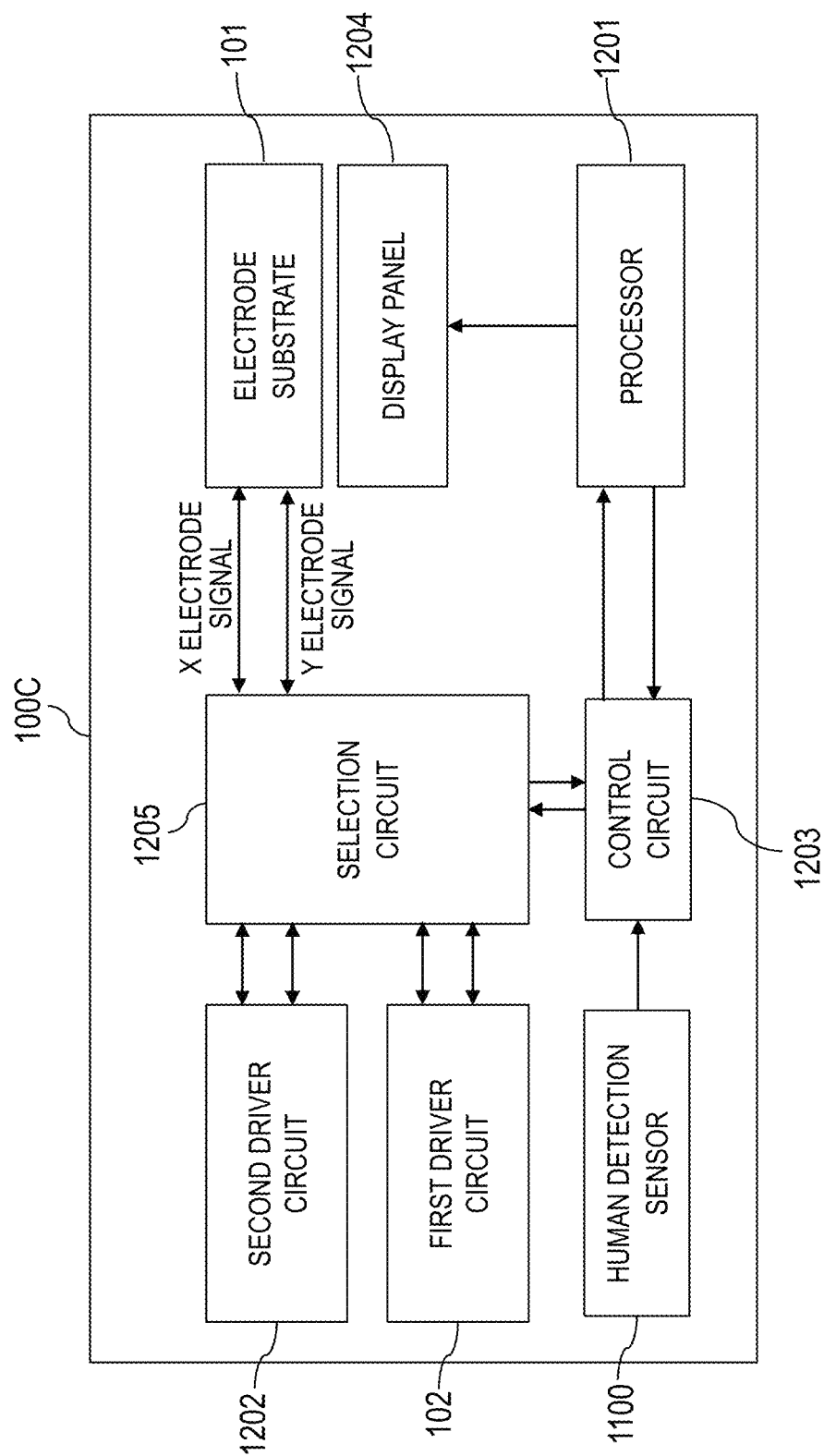
FIG. 12 is a block diagram showing a configuration example of an electronic apparatus according to Embodiment 3.

FIG. 12 is a block diagram showing a configuration example of an electronic apparatus 100C according to Embodiment 3. The electronic apparatus 100C has an electrode substrate 101, a driver circuit 102 (hereinafter referred to as a first driver circuit 102), a processor 1201, a second driver circuit 1202, a selection circuit 1205, a control circuit 1203, and a display panel 1204.

The electrode substrate 101 functions as an ozone source or a touch sensor. Specifically, if driving is performed using the first driver circuit 102 of FIG. 12, for example, then the electrode substrate 101 functions as an ozone source as indicated in Embodiment 1, and if driving is performed using the second driver circuit 1202, then the electrode substrate 101 functions as a touch sensor.

The selection circuit 1205 connects the first driver circuit 102 to the electrode substrate 101 or connects the second driver circuit 1202 to the electrode substrate 101 according to a selection command from the control circuit 1203.

Figure 13:
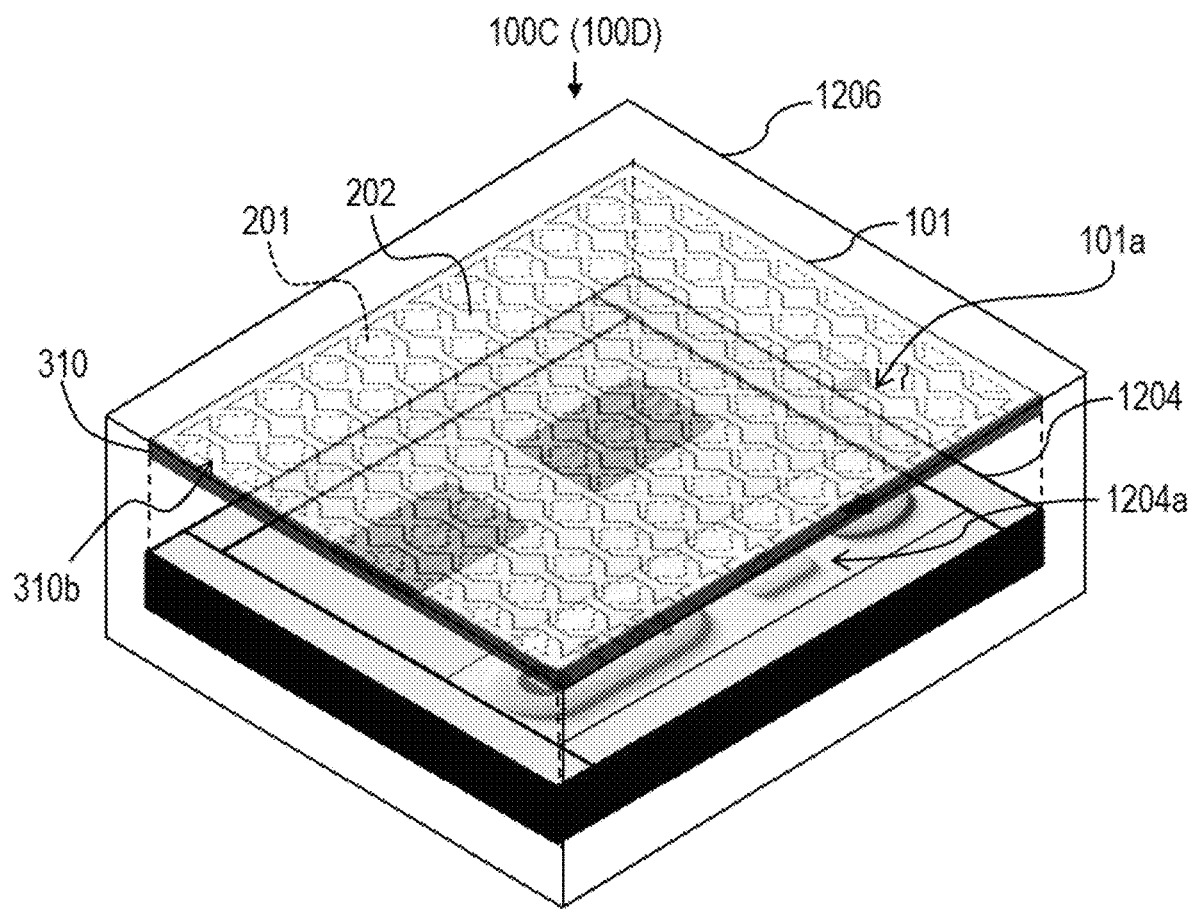
FIG. 13 is a perspective view showing an example of the electronic apparatus 100C according to Embodiment 3.

FIG. 13 is a perspective view showing an example of the electronic apparatus 100C according to Embodiment 3. The electronic apparatus 100C of Embodiment 3 is configured such that the display panel 1204 and the electrode substrate 101 are accommodated inside a case 1206 of the electronic apparatus 100C. Examples of this electronic apparatus 100C include tablets, smartphones, and the like in which the display panel 1204 is a liquid crystal display panel, an OLED (organic light-emitting diode) display panel, or the like.

The electronic apparatus 100C functions as a touch sensor, and thus, the X electrodes 201 and the Y electrodes 202 in the electrode substrate 101 are transparent electrodes. The electrode substrate 101 is configured so as to cover the display panel 1204. Specifically, for example, a second surface 310b of the support substrate 310 of the electrode substrate 101 opposes a display surface 1204a of the display panel 1204. As a result, it is possible to view an image displayed in the display surface 1204a of the display panel 1204 from the contact surface 101a of the electrode substrate 101, and it is possible to generate ozone on the contact surface 101a of the electrode substrate 101.

When the electronic apparatus 100C functions as a touch sensor, the intensity of the electric field generated between the X electrode groups and the Y electrode groups as a result of application thereto of a voltage from terminals 301 and 302 of the electrode substrate 101 is at a level that electric discharge resulting in the generation of ozone does not occur in the space within the single layer of electrodes or in the space between multiple electrode layers, for example. That is, the second driver circuit 1202 applies, to the X electrode groups and the Y electrode groups, a voltage such that the electric field intensity is less than the dielectric breakdown electric field intensity of air, and drives the electrode substrate 101 as a touch sensor. Thus, it is possible to avoid health effects resulting from ozone when operating the touch sensor.

As shown in FIG. 12, the control circuit 1203 controls the selection circuit 1205. Specifically, for example, the control circuit 1203 causes the selection circuit 1205 to select the first driver circuit 102 or the second driver circuit 1202 to be controlled according to a command from the processor 1201 or external input from a sensor (not shown) or human operation.

Also, the processor 1201 outputs the selection command by the selection circuit 1205 indicating the driver circuit to be controlled and outputs a drive command for the display panel 1204 to the control circuit 1203.

The second driver circuit 1202 drives the electrode substrate 101 as a touch sensor. The second driver circuit 1202 is connected to the X electrodes 201 and the Y electrodes 202 via the selection circuit 1205. A capacitance is generated between the X electrodes 201 and the Y electrodes 202 at sections where the X electrodes 201 and the Y electrodes 202 intersect. If a current signal is inputted to the X electrodes 201, an alternating current flows between the X electrodes 201 and the Y electrodes 202.

The second driver circuit 1202 has a current detection unit and uses the current detection unit to detect the alternating current. On the contact surface 101a for contact with a living body, if a living body such as the finger of a person comes into contact with a region opposing the section where the X electrode 201 and the Y electrode 202 intersect, then a capacitance is generated between the X electrode 201 or the Y electrode 202 and the finger, and the capacitance between the X electrode 201 and the Y electrode 202 changes.

If the capacitance between the X electrode 201 and the Y electrode 202 changes, then the alternating current detected by the current detection unit also changes. The X electrodes 201 and the Y electrodes 202 connected to the second driver circuit 1202 are specified by control performed by the control circuit 1203. The control circuit 1203 compares the alternating current detected by the current detection unit to a prescribed threshold, and detects that the capacitance has changed between the X electrode 201 and the Y electrode 202 connected to the second driver circuit 1202. The control circuit 1203 detects the position where the finger has come into contact by identifying the X electrode 201 and the Y electrode 202 connected to the second driver circuit 1202 when the capacitance has changed.

The contact position is a region on the contact surface 101a opposing the section where the X electrode 201 and the Y electrode 202 connected to the second driver circuit 1202 intersect with each other. The control circuit 1203 outputs the detection signal indicating the contact position to the processor 1201. In this manner, the electronic apparatus 100C detects the contact position on the contact surface 101a through mutual capacitance.

The processor 1201 drives the display panel 1204 upon acquiring the detection signal. The processor 1201 may drive the display panel 1204 while the detection signal is being acquired, or in other words, when the contact surface 101a is being touched by a finger, and stop driving the display panel 1204 when the detection signal is no longer being acquired. Also, the processor 1201 may drive the display panel 1204 for a prescribed time from when the detection signal was acquired and stop driving the display panel 1204 after the prescribed time has elapsed. Additionally, the processor 1201 may stop driving the display panel 1204 according to an external input such as human operation.

In this manner, the electronic apparatus 100C of Embodiment 3 can selectively drive the electrode substrate 101 as an ozone source or a touch sensor. If driving the electrode substrate 101 as an ozone source, the contact surface 101a of the electrode substrate 101 can be disinfected by ozone. When the electrode substrate 101 is driven as a touch sensor, it is possible to execute a touch operation on the clean contact surface 101a that has been disinfected by ozone.

When driven as a touch sensor, the intensity of the electric field generated between electrodes due to the input of a current signal is sufficiently less than the intensity at which dielectric breakdown would occur in the air, and thus, no ozone is generated. Thus, it is possible to avoid health effects resulting from ozone when operating the touch sensor.

Also, a configuration like that of Embodiment 2 in which a human detection sensor 1100 is connected to the control circuit 1203 may be adopted. In this manner, if a living body is not present in the vicinity of the electrode substrate 101 of the electronic apparatus 100C, then the human detection sensor 1100 does not output the detection signal regarding detection of a living body to the control circuit 1203, and the control circuit 1203 causes the selection circuit 1205 to select the first driver circuit 102. As a result, the first driver circuit 102 applies a voltage to the X electrodes 201 and the Y electrodes 202 so as to generate ozone. Thus, the electronic apparatus 100C can disinfect the surface 101a of the electrode substrate 101 if a living body is not present in the vicinity of the electrode substrate 101 of the electronic apparatus 100C.

On the other hand, if a living body approaches the vicinity of or comes into contact with the electrode substrate 101 of the electronic apparatus 100C, then the human detection sensor 1100 outputs the detection signal regarding detection of the living body to the control circuit 1203, and the control circuit 1203 causes the selection circuit 1205 to select the second driver circuit 1202. As a result, the first driver circuit 102 stops the application of voltage to the X electrodes 201 and the Y electrodes 202, and the second driver circuit 1202 drives the electrode substrate 101 as a touch sensor by outputting an alternating current signal to the X electrode 201.

Thus, the electronic apparatus 100C can be used as a touch sensor in which the contact surface 101a has been subjected to a disinfection process if a living body is present in the vicinity of the electrode substrate 101 of the electronic apparatus 100C.

Embodiment 4

Next, Embodiment 4 will be described. Embodiment 4 is an example in which the driver circuit of the electronic apparatus 100 C of Embodiment 3 additionally drives the electrode substrate 101 as a tactile presentation panel. A tactile presentation panel is a panel that presents, to a live body, a tactile sensation such as a haptic sensation, a pressure sensation, or a vibration sensation. The surface of the insulating film 312 layered on the electrode substrate 101 is a contact surface 101a for contact by a living body in the touch sensor and the tactile presentation panel. In Embodiment 4, the same components as those of Embodiments 1 to 3 are assigned the same reference characters and descriptions thereof are omitted.

Figure 14:
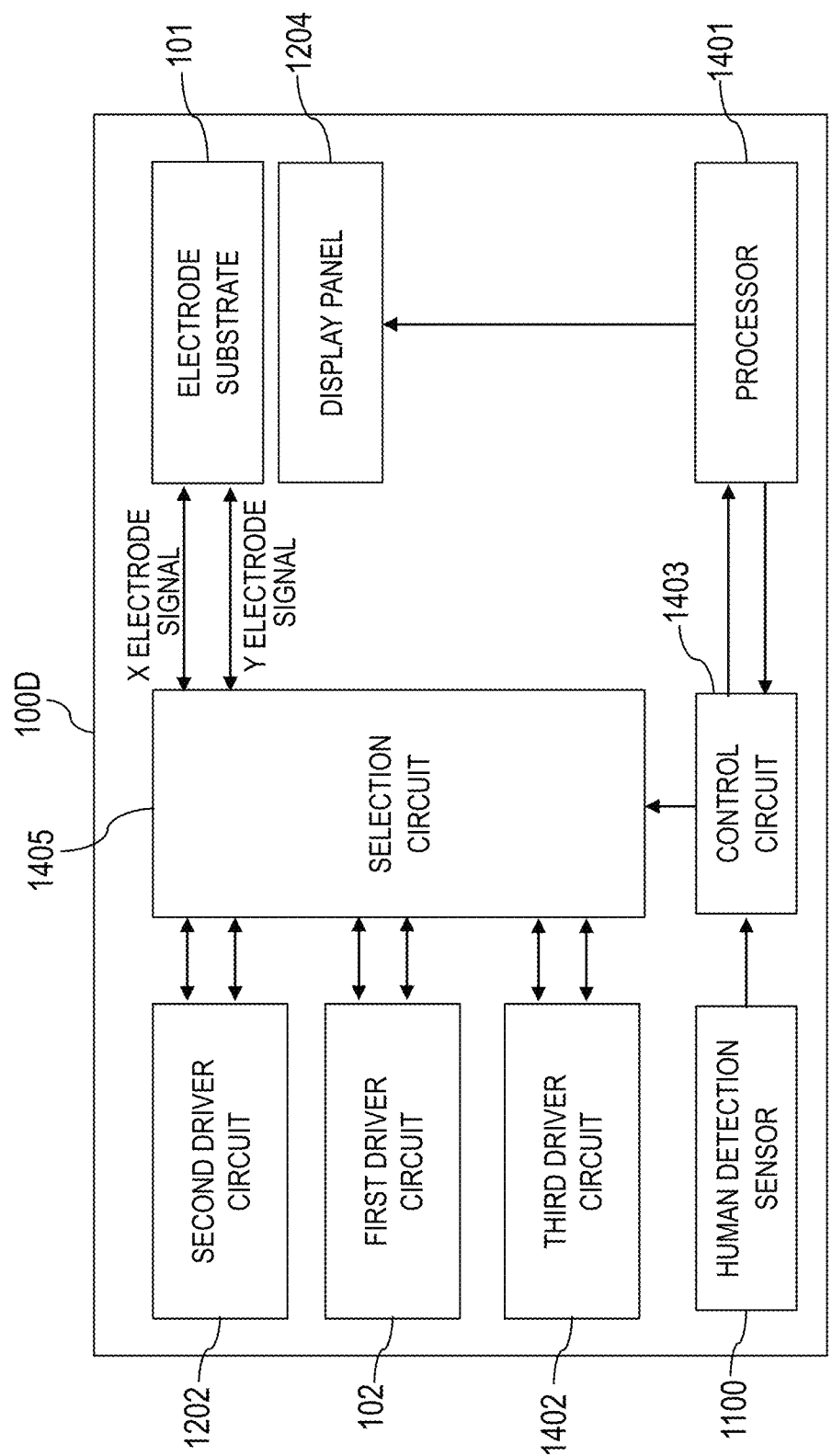
FIG. 14 is a block diagram showing a configuration example of an electronic apparatus according to Embodiment 4.

FIG. 14 is a block diagram showing a configuration example of an electronic apparatus 100D according to Embodiment 4. The electronic apparatus 100D of Embodiment 4 has an electrode substrate 101, a first driver circuit 102, a processor 1401, a second driver circuit 1202, a third driver circuit 1402, a selection circuit 1405, a control circuit 1403, and a display panel 1204. The third driver circuit 1402 drives the electrode substrate 101 as a tactile presentation panel. Examples of the electronic apparatus 100D of Embodiment 4 include a tablet, a smartphone, or the like shown in FIG. 13.

The electrode substrate 101 is provided at a position opposing the display surface 1204a of the display panel 1204, and functions as an ozone source, a touch sensor, or a tactile presentation panel. Specifically, if driving is performed using the first driver circuit 102 of FIG. 14, for example, then the electrode substrate 101 functions as an ozone source as indicated in Embodiment 1, if driving is performed using the second driver circuit 1202, then the electrode substrate 101 functions as a touch sensor as indicated in Embodiment 3, and if driving is performed using the third driver circuit 1402, then the electrode substrate 101 functions as the tactile presentation panel.

The selection circuit 1405 connects the first driver circuit 102 to the electrode substrate 101, connects the second driver circuit 1202 to the electrode substrate 101, or connects the third driver circuit 1402 to the electrode substrate 101 according to a selection command from the control circuit 1403.

The control circuit 1403 controls the selection circuit 1405. Specifically, for example, the control circuit 1403 causes the selection circuit 1405 to select the first driver circuit 102, the second driver circuit 1202, or the third driver circuit 1402 to be controlled according to a command from the processor 1401 or external input from a sensor (not shown) or human operation.

Also, the processor 1401 outputs the selection command by the selection circuit 1405 indicating the driver circuit to be controlled and, similar to Embodiment 3, outputs a drive command for the display panel 1204 to the control circuit 1403 if the second driver circuit 1202 drives the electrode substrate 101 as a touch sensor.

The second driver circuit 1202 is connected to some X electrodes 201 and some Y electrodes 202 through switching performed by the selection circuit 1405, for example. The third driver circuit 1402 is connected to the remaining X electrodes 201 and the remaining Y electrodes 202 that are not connected to the second driver circuit 1202 through switching performed by the selection circuit 1405, for example.

The third driver circuit 1402 independently drives the X electrodes 201 and the Y electrodes 202 of the electrode substrate 101. In the third driver circuit 1402, the circuit that drives the X electrodes 201 is referred to as an X electrode driver circuit, and the circuit that drives the Y electrode 202 is referred to as a Y electrode driver circuit.

The X electrode driver circuit is connected to the X electrodes 201 and generates an alternating current voltage at a first frequency f1. The Y electrode driver circuit is connected to the Y electrodes 202 and generates an alternating current voltage at a second frequency f2. The alternating current voltage at the first frequency f1 and the alternating current voltage at the second frequency f2 are voltages that do not generate ozone, or in other words, voltages by which the electric field intensity is less than the dielectric breakdown electric field intensity of air.

The tactile presentation panel (electrode substrate 101) presents a tactile sensation at the contact surface 101a by operating the X electrode driver circuit and the Y electrode driver circuit. When the user's finger touches the contact surface 101a, the finger opposes the X electrodes 201 or the Y electrodes 202, with the insulating film 312 of the electrode substrate 101 therebetween, and is equivalent to an electrode connected to ground (GND) via a prescribed impedance.

When a voltage is applied to the X electrodes 201 or the Y electrodes 202, an attractive force resulting from static electricity (electrostatic force) is generated between the X electrodes 201 or Y electrodes 202 and the finger. When an alternating current voltage is applied, the electrostatic force periodically changes. As the electrostatic force changes, the frictional force between the contact surface 101a and the finger periodically changes. As the user's finger is traced over the contact surface 101a, the frictional force felt by the finger periodically changes, resulting in the user perceiving a tactile sensation.

Past research has revealed that if the frequency of the alternating current voltage is greater than 5 Hz and less than 500 Hz, a tactile sensation is perceived, whereas if the frequency does not fall within this range, a tactile sensation is not perceived.

Also, if an alternating current voltage at the first frequency f1 is applied to the X electrodes 201 and an alternating current voltage at the second frequency f2 is applied to the Y electrodes 202, then the electrostatic force changes at the first frequency f1 and the second frequency f2. Additionally, a beat is generated in which the electrostatic force changes at a frequency equal to the difference between the first frequency f1 and the second frequency f2.

Past research has revealed that if the frequency of the beat is greater than 10 Hz and less than 1000 Hz, a tactile sensation resulting from the beat is perceived, whereas if the frequency of the beat does not fall within this range, a tactile sensation resulting from the beat is not perceived.

In Embodiment 4, the first frequency f1 and the second frequency f2 are set such that both the first frequency f1 and the second frequency f2 are 500 Hz or greater, and the absolute value of the difference between the first frequency f1 and the second frequency f2 is greater than 10 Hz and less than 1000 Hz. The first frequency f1 is set to 1000 Hz and the second frequency f2 is set to 1240 Hz, for example.

In this manner, the electronic apparatus 100D of Embodiment 4 can selectively drive the electrode substrate 101 as an ozone source, a touch sensor, or a tactile presentation panel. As a result, if driving the electrode substrate 101 as an ozone source, the contact surface 101a of the electrode substrate 101 can be disinfected. When the electrode substrate 101 is driven as a touch sensor or a tactile presentation panel, it is possible for the user to perceive a tactile sensation on the clean contact surface 101a that has been disinfected by ozone. When driven as a tactile presentation panel, the intensity of the electric field generated between electrodes due to application of a voltage is sufficiently less than the intensity at which dielectric breakdown would occur in the air. Thus, ozone is not generated, and therefore, it is possible to avoid health effects resulting from ozone when the user touches the tactile presentation panel.

Also, a configuration like that of Embodiment 2 in which a human detection sensor 1100 is connected to the control circuit 1403 may be adopted. In this manner, if a living body is not present in the vicinity of the electrode substrate 101 of the electronic apparatus 100D, then the human detection sensor 1100 does not output the detection signal regarding detection of a living body to the control circuit 1403, and the control circuit 1403 causes the selection circuit 1405 to select the first driver circuit 102.

As a result, the first driver circuit 102 applies a voltage to the X electrodes 201 and the Y electrodes 202 so as to generate ozone. Thus, the electronic apparatus 100D can disinfect the surface 101a of the electrode substrate 101 if a living body is not present in the vicinity of the electrode substrate 101 of the electronic apparatus 100D.

On the other hand, if a living body approaches the vicinity of or comes into contact with the electrode substrate 101 of the electronic apparatus 100D, then the human detection sensor 1100 outputs the detection signal regarding detection of the living body to the control circuit 1403, and the control circuit 1403 causes the selection circuit 1405 to select the second driver circuit 1202 and/or the third driver circuit 1402.

As a result, the first driver circuit 102 stops the application of voltage to the X electrodes 201 and the Y electrodes 202, the second driver circuit 1202 drives the electrode substrate 101 as a touch sensor by outputting an alternating current signal to the X electrode 201, and the third driver circuit 1402 drives the electrode substrate 101 as a touch sensor by outputting an alternating current signal to the X electrode 201 and drives the electrode substrate 101 as a tactile presentation panel by applying a voltage to the X electrode 201 or the Y electrode 202.

Thus, the electronic apparatus 100D can be used as a touch sensor and/or a tactile presentation panel in which the contact surface 101a has been subjected to a disinfection process if a living body is present in the vicinity of the electrode substrate 101 of the electronic apparatus 100D.

In Embodiment 4, an example was described in which the electrode substrate 101 is simultaneously driven as a touch sensor and a tactile presentation panel, but the electronic apparatus 100A to 100D may be selectively driven as either one of the touch sensor and the tactile presentation panel. Also, the electronic apparatus 100A to 100D may be configured without the second driver circuit 1202. In this manner, the electronic apparatus 100A to 100D can drive the electrode substrate 101 as an ozone source and a tactile presentation panel.

Embodiment 5

Next, Embodiment 5 will be described. Embodiment 5 is an example in which the electronic apparatuses 100A to 100D of Embodiments 1 to 4 are configured such that voltage is scanned across the X electrodes 201 or the Y electrodes 202 when the electrode substrate 101 generates ozone.

Figure 15:
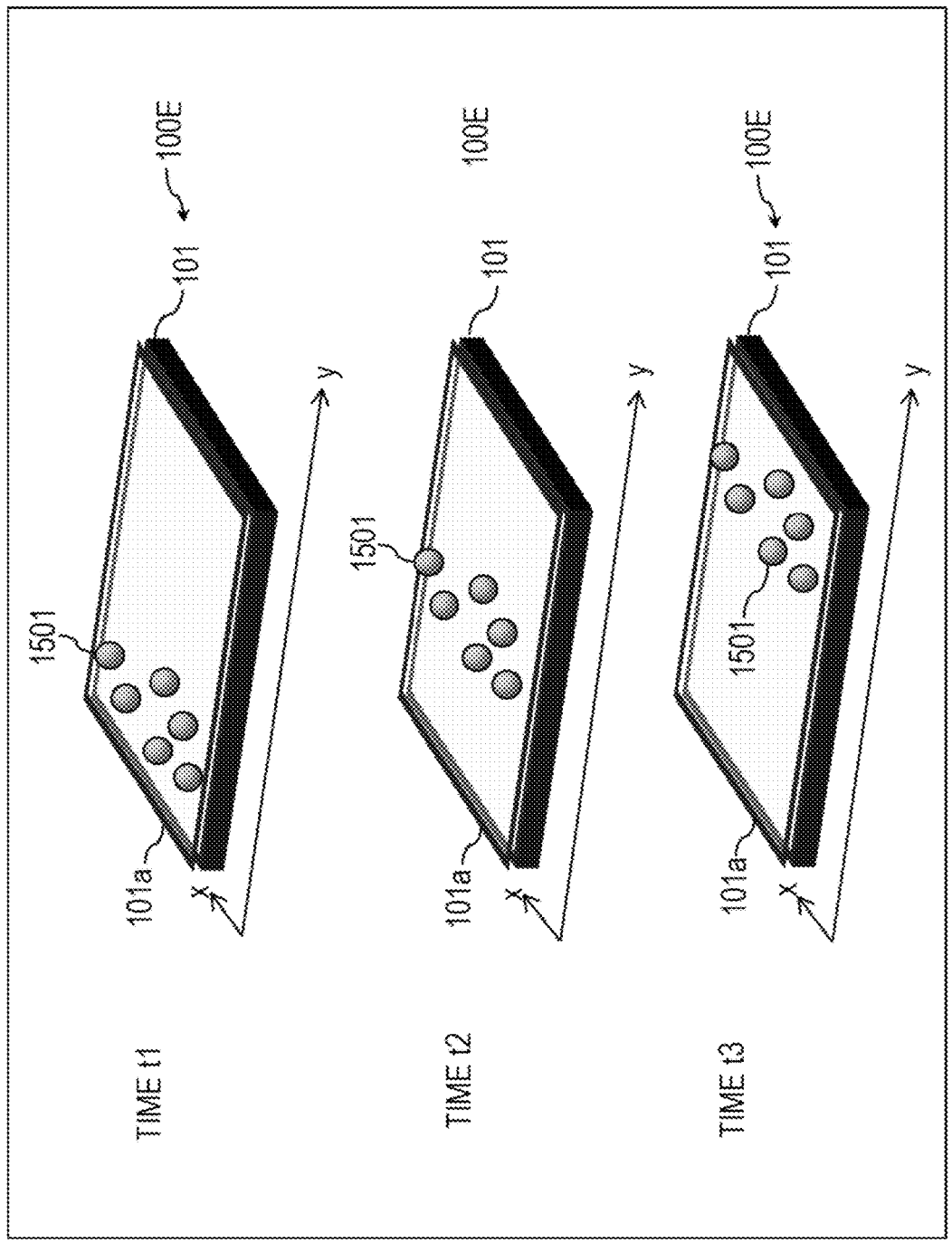
FIG. 15 is a descriptive view showing an example of the scanning performed in an electronic apparatus according to Embodiment 5.

FIG. 15 is a descriptive view showing an example of the scanning performed in an electronic apparatus 100E according to Embodiment 5. As described in Embodiment 1, the electrode substrate 101 has one or more X electrode groups, in which the X electrodes are linked in a beaded configuration in the x direction, that are disposed in the y direction. The Y electrodes 202 are assumed in this case to be connected to ground. The driver circuit sequentially applies voltage starting with the X electrode group on one end and then onward in the y direction.

At a time t1, ozone 1501 is generated at one end in the y direction of the surface 101a of the electrode substrate 101, for example. (B) At a time t2 (>t1), the ozone 1501 is generated at an intermediate position in the y direction of the surface 101a of the electrode substrate 101. (C) At a time t3 (>t2), the ozone 1501 is generated at the other end in the y direction of the surface 101a of the electrode substrate 101, for example.

In this manner, by scanning voltage across the X electrode groups, the distribution of heat produced through the generation of the ozone 1501 on the surface 101a is changed over time, thereby generating convection in air including the ozone 1501.

Also, in FIG. 15, scanning is performed from one end to the other end of the surface 101a in the y direction, but scanning may be performed from an intermediate position to both ends in the y direction. Additionally, in FIG. 15, scanning was performed across the X electrode groups, but the driver circuit 102 may connect the X electrodes 201 to ground and perform scanning in the x direction across Y electrode groups in which the Y electrodes are linked in a beaded configuration in the y direction.

Also, FIG. 15 illustrates a configuration in which voltage is applied to either the X electrodes 201 or the Y electrodes 202, but the driver circuit 102 may select X electrodes 201 and Y electrodes 202 corresponding to a given region on the surface 101a and apply voltage for generating ozone thereto to generate the ozone 1501 in the region.

By limiting the application of voltage to a region in the surface 101a to which a living body could come into contact, for example, it is possible to generate the ozone 1501 in a partial region to perform disinfection, thereby mitigating the generation of the ozone 1501 in a region where disinfection is unnecessary. As a result of mitigating voltage application in regions where disinfection is unnecessary, it is possible to reduce power consumption.

Embodiment 6

Embodiment 6 will be described next. Embodiment 6 is an example in which the electrode substrate 101 functions as a touch sensor without the use of the display medium 104 that displays images. The same components as those of Embodiments 1 to 5 are assigned the same reference characters and descriptions thereof are omitted.

Figure 16A:
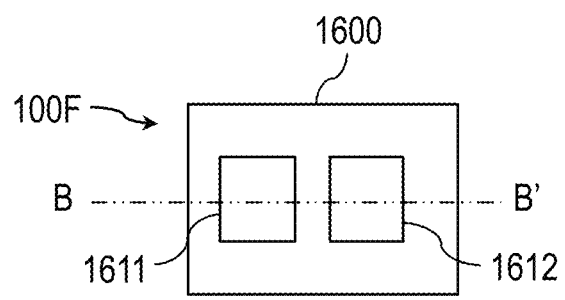
FIGS. 16A and 16B are descriptive views showing an electronic apparatus according to Embodiment 6.
Figure 16B:
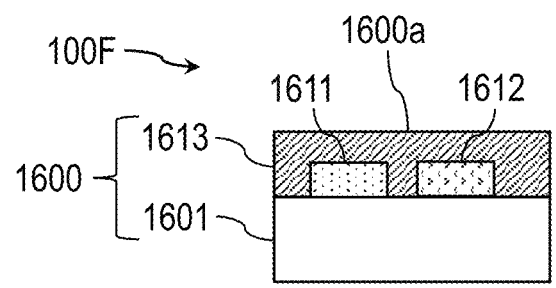

FIGS. 16A and 16B is a descriptive view showing an electronic apparatus 100F according to Embodiment 6. FIG. 16A is a plan view of the electronic apparatus 100F of Embodiment 6. FIG. 16B is a cross-sectional view along the line B-B' in FIG. 16A. The electronic apparatus 100F has an electrode substrate 1600. The electrode substrate 1600 has a support substrate 1601 such as a glass substrate, one X electrode 1611 on the support substrate 1601, one Y electrode 1612 on the support substrate 1601, and an insulating film 1613 that covers the X electrode 1611 and the Y electrode 1612.

The X electrode 1611 and the Y electrode 1612 are disposed on the support substrate 1601 with a prescribed gap (10 μm, for example) therebetween. In other words, the X electrode 1611 and the Y electrode 1612 are in a single layer electrode structure such as that shown in FIG. 3A. Also, the electrode substrate 1600 is driven as an ozone source and a touch sensor.

Figure 17:
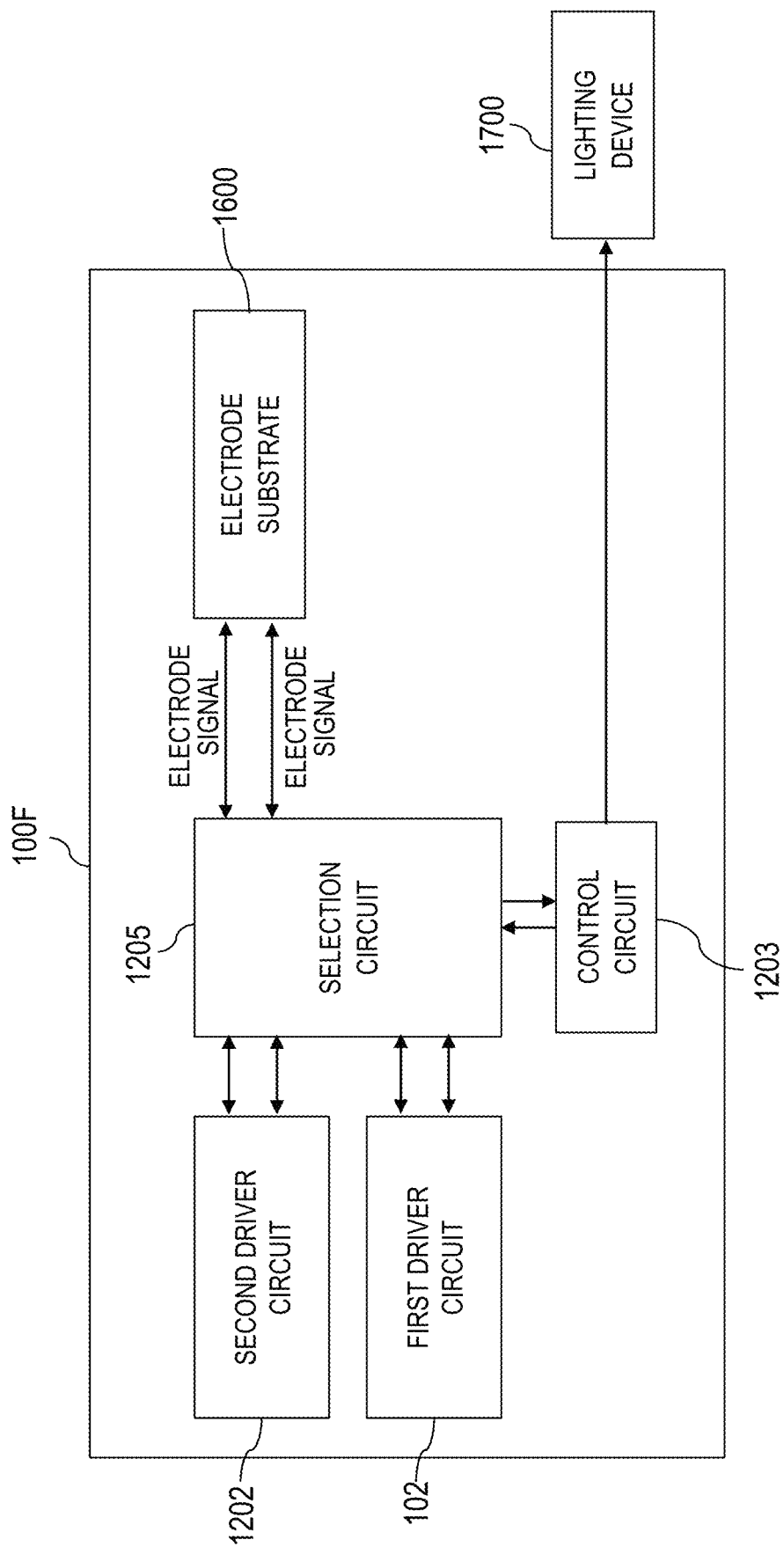
FIG. 17 is a block diagram showing a configuration example of an electronic apparatus according to Embodiment 6.

FIG. 17 is a block diagram showing a configuration example of an electronic apparatus 100F according to Embodiment 6. The electronic apparatus 100F of Embodiment 6 has the electrode substrate 1600, a first driver circuit 102, a second driver circuit 1202, a selection circuit 1205, and a control circuit 1203. Also, a configuration like that of Embodiment 2 in which a human detection sensor 1100 is connected to the control circuit 103 may be adopted.

The electronic apparatus 100F can be used in a light switch, for example. Control for turning the light switch ON or OFF is executed by the control circuit 1203 connected to a lighting device 1700, which is an example of an object to be controlled.

If the second driver circuit 1202 is selected by the selection circuit 1205, for example, then every time a living body such as a finger touches a contact surface 1600a of the electrode substrate 1600 driven as a touch sensor, the electrode substrate 1600 outputs, to the control circuit 1203, a detection signal indicating a contact position where the living body came into contact. Upon receipt of the detection signal, the control circuit 1203 turns the lighting device 1700 ON or OFF.

Specifically, for example, if the control circuit 1203 receives the detection signal in an OFF state, the lighting device 1700 is turned ON, and if the control circuit 1203 receives the detection signal in an ON state, the lighting device 1700 is turned OFF. The lighting device 1700 is not limited to the two states of ON and OFF, and a configuration that allows for periodic switching between three or more states such as brightness (high)->brightness (mid)->brightness (low)->OFF->brightness (high), etc., may be adopted.

On the other hand, if the first driver circuit 102 is selected by the selection circuit 1205, the electrode substrate 1600 driven as an ozone source generates ozone on the contact surface 1600a and disinfects the contact surface 1600a.

Also, the control circuit 1203 causes the selection circuit 1205 to select the first driver circuit 102 and the second driver circuit 1202 according to external input from a sensor (not shown) or human operation. Specifically, a scenario is assumed in which the electronic apparatus 100F is installed in an office as a light switch, for example.

In this case, at a time during the night, a holiday/weekend, or the like such as a prescribed first day/time (8 PM on Fridays, for example) or a prescribed first time (8 PM on weekdays, for example), the control circuit 1203 controls the selection circuit 1205 to switch from driving the first driver circuit 102 to driving the second driver circuit 1202. If, at the time that the switch occurs, the lighting device is ON, the control circuit 1203 turns OFF the lighting device 1700. As a result, in the electronic apparatus 100F, the electrode substrate 1600 generates ozone on the contact surface 1600a and disinfects the contact surface 1600a.

Also, at the start of business or the like such as a prescribed first day/time (7 AM on weekdays, for example), the control circuit 1203 controls the selection circuit 1205 to switch from driving the second driver circuit 1202 to driving the first driver circuit 102. As a result, the electrode substrate 1600 is driven as a touch sensor, and therefore, the lighting device 1700 is switched from OFF to ON as the result of a living body such as a finger touching the contact surface 1600a. Therefore, the control circuit 1203 controls the selection circuit 1205 so as to switch to the first driver circuit 102 when in a non-use period as a touch sensor, and switch to the second driver circuit 1202 when the non-use period elapses.

Thus, according to Embodiment 6, by using the electronic apparatus 100F in a light switch to be touched by people, it is possible to disinfect the contact surface 1600a where the lighting device 1700 is switched ON or OFF while the contact surface 1600a is not used as the light switch.

The shape of the X electrode 1611 and the Y electrode 1612 may be a quadrilateral like that of the X electrodes 201 and the Y electrodes 202, may be a polygon such as that of the X electrodes 901 and the Y electrodes 902 shown in FIG. 9, or may be another shape. Also, the electronic apparatus 100F may be configured to have a plurality of the layered structures shown in FIG. 10. It is possible to increase the electric field generation region by using such electrode shapes and layered structures. Thus, it is possible to improve ozone generation efficiency and reduce power consumption.

Embodiment 7

Next, Embodiment 7 will be described. Embodiment 7 is an example in which a measure to counteract leakage current is applied to the electronic apparatuses 100A to 100F of Embodiments 1 to 6. Leakage current occurs when, in a state where the insulating film 312 is damaged and foreign matter such as water has entered the damaged section, the finger comes in contact with the damaged section and current flows through the finger to the person's body. In an electronic apparatus 100G of Embodiment 7, a structure for suppressing this leakage current is adopted. The same components as those of Embodiments 1 to 6 are assigned the same reference characters and descriptions thereof are omitted.

Figure 18A:
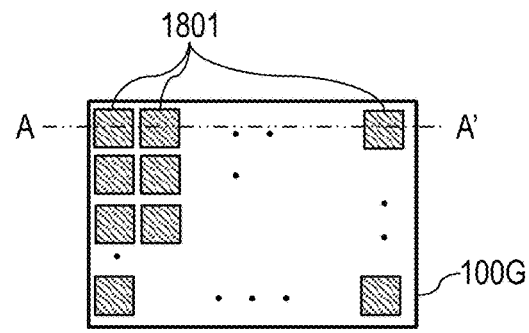
FIGS. 18A to 18C are descriptive views showing an electronic apparatus according to Embodiment 7.
Figure 18B:
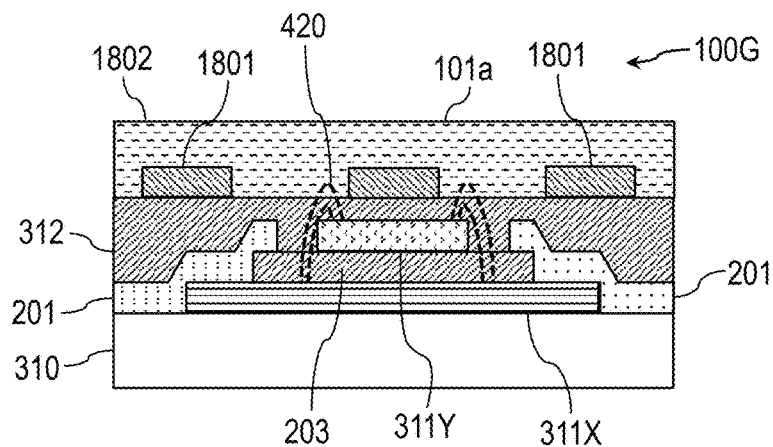
Figure 18C:
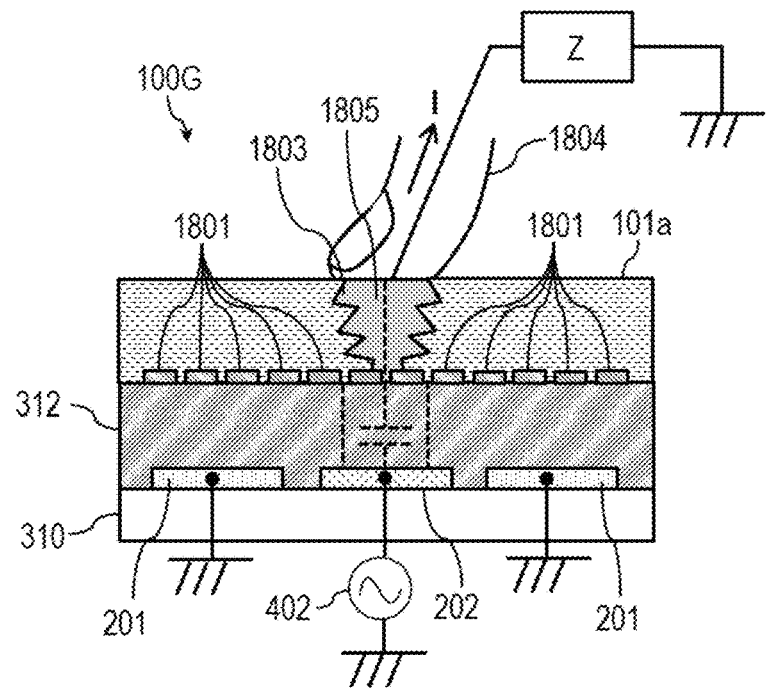

FIGS. 18A to 18C are descriptive views showing an electronic apparatus 100G according to Embodiment 7. FIG. 18A is a plan view of the electronic apparatus 100G of Embodiment 7, FIG. 18B is a cross-sectional view along the line A-A' of FIG. 18A, and FIG. 18C is an operation example of the electronic apparatus 100G of Embodiment 7.

The electronic apparatus 100G has a plurality of floating electrodes 1801 on the insulating film 312. The floating electrodes 1801 can be made of a conductor or semiconductor such as ITO, for example. The floating electrodes 1801 are electrically isolated from each other. The plurality of floating electrodes 1801 are covered by an insulating film 1802. As shown in FIG. 18A, the plurality of floating electrodes 1801 are arranged in a 2-dimensional array, for example.

Each individual floating electrode 1801 forms a capacitor with the opposing X electrode 201 or Y electrode 202. A voltage is induced due to capacitance coupling between the floating electrode 1801 and the opposing X electrode 201 or Y electrode 202. The capacitance of the capacitor formed between each floating electrode 1801 and the opposing X electrode 201 or Y electrode 202 is determined by the area of the floating electrode 1801.

The floating electrodes 1801 are all the same shape and same area. However, the floating electrodes 1801 need not necessarily be the same shape, and may differ in area. In Embodiment 7, the shape of the damaged section formed in the insulating film 1802 is assumed to be substantially cylindrical with a diameter of 3 mm. In this case, the shape of the smallest possible floating electrode 1801 that would encompass the damaged section would be a square with 3 mm sides.

In Embodiment 7, if the shape of each floating electrode 1801 is a square with 3 mm sides, the area of the floating electrode 1801 would be 9 $mm^2$. Adjacent floating electrodes 1801 are arranged in a plane with a 0.5 mm gap therebetween, for example.

The upper surfaces of the plurality of floating electrodes 1801 are covered by the insulating film 1802. The insulating film 1802 is the contact surface 101a that would be directly touched by the user, and prevents contact between the finger 1804 and the floating electrodes 1801. The insulating film 1802 is an acrylic, for example.

FIG. 18C illustrates a state in which a damaged section 1803 reaching down to the floating electrodes 1801 is formed in the insulating film 1802, and a conductive foreign matter 1805 such as water has entered the damaged section 1803. The foreign matter 1805 is in electrical contact with at most four floating electrodes 1801. When the finger 1804 comes in contact with the foreign matter 1805, the electric charge accumulated in the capacitor corresponding to the total area of four floating electrodes 1801 flows to the finger 1804 as a leakage current I.

However, this leakage current is equivalent to the charge accumulated in the four floating electrodes 1801, and thus, is very small. As a result of providing this measure to counteract leakage current to the electronic apparatuses 100 of Embodiments 1 to 6, it is possible to suppress leakage current.

As shown in FIG. 18B, it is preferable that a configuration be adopted in which the floating electrodes 1801 are not provided on the layered electrodes. As a result of this configuration, the electric field 420 generated due to the potential difference between the bridge electrode 311X and the bridge electrode 311Y can reach the air above the insulating film 312 without being blocked by the floating electrodes 1801. Thus, dielectric breakdown can occur in the air, thereby generating ozone.

As described above, in the electronic apparatuses 100A to 100G of Embodiments 1 to 7, the X electrodes 201 and the Y electrodes 202 of the electrode substrate 101 are transparent electrodes, and the electrode substrate 101 is shared by the ozone source and the display medium. Thus, it is possible to attach the display surface of a display device onto the second surface 310b and allow the display surface to be visible through the surface 101a of the electrode substrate 101. As a result, it is possible to view the display surface through the surface 101a, and to maintain sanitation of the surface 101a. Also, it is possible to sanitize the surface 101a with fewer components.

Additionally, in the electronic apparatuses 100A to 100G of Embodiments 1 to 7, the electrode substrate 101 is shared by the ozone source and another function (such as a touch sensor or a tactile presentation device), and thus, when the other function is not in use, it is possible to disinfect the contact surface 101a that would come into contact with a living body when the other function is in use. Thus, it is possible to maintain sanitation of the contact surface 101a without separately providing a disinfectant spray or an ozone generator. Also, it is possible to sanitize the contact surface 101a with fewer components.

According to representative embodiments of the present invention, it is possible to maintain sanitation of surfaces at which images can be viewed and surfaces with which a person could come into contact.

What is claimed is:

1. An electronic apparatus, comprising:
an electrode substrate that has a transparent first electrode and a transparent second electrode that are provided on one surface of a transparent insulating substrate, and an insulating film that electrically insulates the first electrode from the second electrode, the electrode substrate being configured so as to cover a surface of a display medium where an image is displayed; and
a driver circuit that is connected to the electrode substrate and generates an electric field between the first electrode and the second electrode by applying a voltage to the first electrode and the second electrode,
wherein the electrode substrate generates ozone over the electrode substrate according to an applied voltage from the driver circuit.

2. The electronic apparatus according to claim 1,
wherein the second electrode, the insulating film, and the first electrode are layered in the stated order on the transparent insulating substrate, and
wherein at least a portion of the edge of the first electrode overlaps the second electrode in a plan view.

3. The electronic apparatus according to claim 1,
wherein a peak value of an intensity of the electric field over the electrode substrate is greater than or equal to a dielectric breakdown electric field intensity of air.

4. The electronic apparatus according to claim 3,
wherein the peak value of the intensity of the electric field on the insulating film is less than a dielectric breakdown electric field intensity of the insulating film.

5. The electronic apparatus according to claim 1,
wherein first electrode groups, in which a plurality of the first electrodes having a specific shape that are connected by a first connection unit are arrayed in a first direction, are arranged in a second direction so as to extend in parallel with each other,
wherein second electrode groups, in which a plurality of the second electrodes having a specific shape that are connected by a second connection unit are arrayed in the second direction, are arranged in the first direction so as to extend in parallel with each other, and
wherein, in the first electrode group and the second electrode group, the first connection unit and the second connection unit are layered on each other with the insulating film interposed therebetween.

6. The electronic apparatus according to claim 5,
wherein the specific shape of either of the first electrodes and the second electrodes is a shape having a first protrusion that projects from an interior to an exterior of said electrodes, and
wherein the specific shape of the other of the first electrodes and the second electrodes is a shape having a first recess that covers the periphery of the first protrusion via the insulating film.

7. An electronic apparatus, comprising:
an electrode substrate that has a transparent first electrode and a transparent second electrode that are provided on one surface of a transparent insulating substrate, and an insulating film that electrically insulates the first electrode from the second electrode, the electrode substrate being configured so as to cover a surface of a display medium where an image is displayed; and
a driver circuit that is connected to the electrode substrate and generates an electric field between the first electrode and the second electrode by applying a voltage to the first electrode and the second electrode,
a detection unit that detects the presence of a living body on a surface of the electrode substrate and outputs a signal; and
a control circuit that controls the driver circuit on the basis of the signal from the detection unit,
wherein the control circuit applies a voltage between the first electrode and the second electrode if there is no signal from the detection unit, and
wherein the electrode substrate generates ozone over the electrode substrate according to an applied voltage from the driver circuit.

8. An electronic apparatus, comprising:
an electrode substrate that has a transparent first electrode and a transparent second electrode that are provided on one surface of a transparent insulating substrate, and a first insulating film that electrically insulates the first electrode from the second electrode;
a display medium in which a display surface that displays an image is covered by the electrode substrate;
a first driver circuit that is connected to the electrode substrate and drives the electrode substrate as an ozone source by applying a voltage to the first electrode and the second electrode;

a second driver circuit that is connected to the electrode substrate and drives the electrode substrate as a touch sensor by applying a voltage to the first electrode and the second electrode; and a selection circuit that switches between the first driver circuit and the second driver circuit.

9. The electronic apparatus according to claim 8,
wherein a peak value of an intensity of the electric field over the electrode substrate is greater than or equal to a dielectric breakdown electric field intensity of air.

10. The electronic apparatus according to claim 8,
wherein the second driver circuit applies a voltage to the first electrode and the second electrode to a degree that ozone is not generated over the electrode substrate.

11. The electronic apparatus according to claim 8, further comprising:
a third driver circuit that drives the electrode substrate such that a tactile sensation can be presented on a contact surface of the electrode substrate,
wherein the selection circuit can select between the first driver circuit, the second driver circuit, and the third driver circuit.

12. The electronic apparatus according to claim 11,
wherein first electrode groups, in which a plurality of the first electrodes having a rectangular shape that are connected by a first connection unit are arrayed in a first direction, are arranged in a second direction so as to extend in parallel with each other,
wherein second electrode groups, in which a plurality of the second electrodes having a specific shape that are connected by a second connection unit are arrayed in the second direction, are arranged in the first direction so as to extend in parallel with each other,
wherein, in the first electrode group and the second electrode group, the first connection unit and the second connection unit are layered on each other with the first insulating film interposed therebetween, and
wherein the third driver circuit applies a voltage signal at a first frequency to a specific first electrode group, among the first electrode groups, that corresponds to a target region inputted from an external source, applies a voltage signal at a second frequency to a specific second electrode group, among the second electrode groups, that corresponds to the target region, and generates an electric beat vibration to the target region according to an absolute value of a difference between the first frequency and the second frequency.

13. The electronic apparatus according to claim 1,
wherein a plurality of combinations of the first electrode and the second electrode are arrayed on the electrode substrate, and
wherein the driver circuit drives some combinations among the plurality of combinations.

14. The electronic apparatus according to claim 13,
wherein the driver circuit drives a first combination and a second combination, among the plurality of combinations, at differing timings.

15. The electronic apparatus according to claim 14,
wherein the driver circuit drives at least one of the first electrode and the second electrode in a prescribed scanning direction, among the plurality of combinations.

16. The electronic apparatus according to claim 11, further comprising:
a plurality of floating electrodes that are disposed on the first insulating film, and that are electrically isolated from each other; and
a second insulating film that covers the plurality of floating electrodes.

17. An electronic apparatus, comprising:
an electrode substrate that has a transparent first electrode and a transparent second electrode that are provided on one surface of a transparent insulating substrate, and an insulating film that electrically insulates the first electrode from the second electrode;
a first driver circuit that is connected to the electrode substrate and drives the electrode substrate as an ozone source by applying a voltage to the first electrode and the second electrode;
a second driver circuit that is connected to the electrode substrate and drives the electrode substrate as a touch sensor by applying a voltage to the first electrode and the second electrode; and
a selection circuit that switches between the first driver circuit and the second driver circuit.

18. The electronic apparatus according to claim 17, further comprising:
a control circuit that is connected to an item to be controlled, and that executes selection control of the selection circuit and control of the item to be controlled,
wherein the control circuit controls the item to be controlled if a detection signal indicating detection of contact by a living body is outputted from the electrode substrate that is driven as the touch sensor by the second driver circuit.

19. The electronic apparatus according to claim 18,
wherein the control circuit controls the selection circuit so as to switch to the first driver circuit when the electrode substrate is in a non-use period as the touch sensor, and so as to switch to the second driver circuit when the non-use period elapses.

* * * * *